(12) United States Patent
Retterer et al.

(10) Patent No.: US 9,630,178 B2
(45) Date of Patent: Apr. 25, 2017

(54) METHOD FOR PREPARING SMALL VOLUME REACTION CONTAINERS

(75) Inventors: Scott T. Retterer, Knoxville, TN (US); Mitchel J. Doktycz, Knoxville, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 1582 days.

(21) Appl. No.: 13/050,478

(22) Filed: Mar. 17, 2011

(65) Prior Publication Data

US 2012/0003675 A1 Jan. 5, 2012

Related U.S. Application Data

(60) Provisional application No. 61/314,869, filed on Mar. 17, 2010.

(51) Int. Cl.
| | |
|---|---|
| *B01L 3/00* | (2006.01) |
| *B81C 1/00* | (2006.01) |
| *B82Y 40/00* | (2011.01) |
| *C12P 21/02* | (2006.01) |

(52) U.S. Cl.
CPC ... *B01L 3/502746* (2013.01); *B01L 3/502707* (2013.01); *B81C 1/00126* (2013.01); *B82Y 40/00* (2013.01); *C12P 21/02* (2013.01); *B01L 2300/0816* (2013.01); *B01L 2300/0819* (2013.01); *B01L 2300/0867* (2013.01); *B01L 2300/0896* (2013.01); *B01L 2400/0472* (2013.01); *B81B 2201/06* (2013.01)

(58) Field of Classification Search
CPC ............ B01L 3/5027; B01L 3/502756; B01L 2300/0819; B01L 2300/161

USPC ...... 422/68.1, 502, 503, 504, 506, 507, 547, 422/551, 552
See application file for complete search history.

(56) References Cited

U.S. PATENT DOCUMENTS

| | | | | |
|---|---|---|---|---|
| 6,143,247 A | * | 11/2000 | Sheppard et al. | 422/63 |
| 6,143,248 A | * | 11/2000 | Kellogg et al. | 422/72 |
| 6,296,020 B1 | * | 10/2001 | McNeely et al. | 137/806 |
| 7,641,863 B2 | | 1/2010 | Doktycz et al. | |
| 2004/0173506 A1 | | 9/2004 | Doktycz et al. | |

(Continued)

FOREIGN PATENT DOCUMENTS

WO WO 2008/108862 * 9/2008 ............ 422/507

OTHER PUBLICATIONS

Hung et al. "A novel high aspect ratio microfluidic design to provide a stable and uniform microenvironment for cell growth in a high throughput mammalian cell culture array". Lab Chip, 2005, vol. 5, pp. 44-48.*

(Continued)

*Primary Examiner* — Jill Warden
*Assistant Examiner* — Dwayne K Handy
(74) *Attorney, Agent, or Firm* — Quarles & Brady LLP

(57) ABSTRACT

Engineered reaction containers that can be physically and chemically defined to control the flux of molecules of different sizes and charge are disclosed. Methods for constructing small volume reaction containers through a combination of etching and deposition are also disclosed. The methods allow for the fabrication of multiple devices that possess features on multiple length scales, specifically small volume containers with controlled porosity on the nanoscale.

33 Claims, 24 Drawing Sheets

(56) References Cited

U.S. PATENT DOCUMENTS

2007/0161028 A1* 7/2007 Schwartz et al. .................. 435/6
2009/0311190 A1* 12/2009 Gracias et al. ................ 424/9.3

OTHER PUBLICATIONS

Noireaux et al., Proc. Natl. Acad. Sci. U. S. A., 2004, 101, 17669-17674.
Murtas et al., Biochem. Biophys. Res. Commun., 2007, 363, 12-17.
Karlsson et al., J. Phys. Chem. B, 2005, 109, 1609-1617.
Song, et al., Angew. Chem., Int. Ed., 2006, 45, 7336-7356.
Fowlkes, et al., Nanotechnology, 2008, 19.
Retterer, et al., Carbon, 2008, 46, 1378-1383.
Hasty, et al., Nature, 2002, 420, 224-230.
Purnick et al., Nat. Rev.Mol. Cell Biol., 2009, 10, 410-422.

* cited by examiner

METHOD FOR PREPARING SMALL VOLUME REACTION CONTAINERS

CROSS-REFERENCES TO RELATED APPLICATIONS

This application claims priority from U.S. Patent Application No. 61/314,869 filed Mar. 17, 2010.

STATEMENT REGARDING FEDERALLY SPONSORED RESEARCH

This invention was made with government support under Contract No. DE-AC05-00OR22725 awarded by the U.S. Department of Energy. The government has certain rights in the invention.

BACKGROUND OF THE INVENTION

1. Field of the Invention

This invention relates to reaction containers that can be physically and chemically defined to control the flux of molecules of different sizes and charge. The invention also relates to methods for constructing small volume reaction containers through etching or a combination of etching and deposition. The methods allow for the fabrication of multiple devices that possess features on multiple length scales, specifically small volume containers with controlled porosity on the nanoscale. The invention further relates to the use of the reaction containers in sensing and the production or conversion of biological materials.

2. Description of the Related Art

Biochemical reactions such as protein synthesis and enzymatic conversion are fundamental to the function of living systems and are vital tools in industry and research. As our understanding of these reactions, and the living cellular systems in which they are carried out, has grown, the importance of cellular organization and efficiencies achieved by operating at the cellular scale have become more apparent. This, combined with a desire to understand "what constitutes life", has led to efforts to create synthetic cellular-scale containers, cell mimics, in which basic biochemical processes can be sustained.

With respect to cell mimics, U.S. Pat. No. 7,641,863 and corresponding U.S. Patent Application Publication No. 2004/0173506 describe nanoengineered structures for controlling material transport (e.g., molecular transport). In one example form, the structure for controlling transport of a material includes a membrane enclosure having at least one outer wall and at least a portion of one outer wall comprises a plurality of spaced apart fibers having a fiber width of 250 nanometers or less. A material is located within the membrane enclosure, and the material has a physical or chemical property such that the material is selectively restricted by the fibers from passing from the inside to the outside of the enclosure.

The structure includes means for controlling transport of the material both into and out of the membrane enclosure. In one version of the structure, chemical derivatization of the fibers may be undertaken to affect the diffusion limits or effect selective permeability or facilitated transport. For example, a coating can be applied to at least a portion of the fibers. In another embodiment, individually addressable carbon nanofibers can be integrated with the membrane to provide an electrical driving force for material transport. U.S. Pat. No. 7,641,863 is incorporated herein by reference.

Chemical reactions within the cell depend on the cellular membrane, as it (1) defines the spatial extent (volume) of the cell, and (2) regulates the transfer of reactants and products between the cellular reaction volume and its surroundings. Within the small volume of the cell, passive transport of molecules via diffusion is rapid and facilitates the efficient mixing of molecules within the cell. Furthermore, because the cell can contain only a limited, small number of molecules, small changes in the numbers of molecules can lead to drastic changes in concentration within the cell. Such changes can lead to significant alterations in cellular function and fate. Beyond its passive role as a "container," the cellular membrane plays a dynamic role in affecting internal concentrations by regulating the exchange of materials between the internal volume of the cell and the external microenvironment, both in concert with and against electrical and chemical potentials.

A growing body of work has examined the efficacy of biomimetic systems for carrying out biological processes in micro/cellular-scale systems. Such work includes the solution synthesis of liposomes and vesicles, serial creation of surface bound, single and networked vesicles, and microfluidic generation of cellular-scale droplets formed in multiphase fluidics and inorganic microscale containers. In general, these approaches have all sought to capture the basic function of the cellular membrane, defining small volumes in which diffusive transport is efficient, and the transfer of materials between the internal reaction volume and the external environment is regulated.

The use of vesicle bioreactors for carrying out cell-free transcription and translation for the production of green fluorescent protein (GFP) has been examined, and it has been found that reactions could be sustained for up to four days with the incorporation of an α-hemolysin pore that made the membrane permeable to external reactants. (See, Noireaux et al., *Proc. Natl. Acad. Sci. U.S.A.*, 2004, 101, 17669-17674.) In a similar work, the expression of enhanced GFP in liposomes using a specific and well-defined set of minimal enzymes was successfully carried out. (See, Murtas et al., *Biochem. Biophys. Res. Commun.*, 2007, 363, 12-17). Despite the success of these solution based approaches, the isolation of individual vesicles for monitoring individual reactions (addressability) and potential difficulties involving long term stability and storage of such vesicles in extreme conditions of tonicity (osmolarity), pH and temperature remain a challenge for the integration of these vesicle reactors into a sensing and actuation platform.

A related work (Karlsson et al., *J. Phys. Chem. B,* 2005, 109, 1609-1617), utilized vesicles formed on surfaces, which could be connected by small nanoscale vesicle channels, to create small reaction volumes and networks. Because each volume could be formed using a different microinjection pipette, each could be filled with individual reagents and scaled according to the desired function. The technique was highly effective, and allowed tuning of mass transport from one volume to the other by controlling the interconnecting channel width and length, establishing a predictable concentration gradient (flux) between reaction containers. The approach demonstrates improved addressability over conventional liposome and vesicle based approaches, allowing the progression of a reaction within a single volume to be monitored over time. However, the serial nature by which the reaction volumes are created, coupled with their inability to be stored over long periods makes the creation and use of many identical reaction volumes difficult. Furthermore, like vesicles synthesized in solution, the approach is likely to suffer from poor stability under more extreme reaction conditions.

Advances in soft lithography have made the study of reactions in microscale droplets created within lab-on-a-chip (LOC) systems accessible. Significant contributions have been made in the development and study of droplet generating and mixing systems. The exquisite control of droplet size and mixing afforded by microfluidics has even facilitated studies of reaction kinetics in sub-cellular-scale droplets. A review of the topic of reactions in droplets, highlighting the techniques and describing various applications for microfluidic droplet generation and mixing can be found at Song, et al., *Angew. Chem., Int. Ed.,* 2006, 45, 7336-7356. While droplet-based microfluidics provide exquisite control of single reaction volumes, the multiphase nature of these systems can make the exchange of materials between reaction containers difficult.

Therefore, there is a need for a cellular-scale reaction container that can be spatially addressed for monitoring and filling, while allowing both the storage and exchange of chemical information across the reactor membrane.

SUMMARY OF THE INVENTION

Engineers seek to use biological design principles to manipulate information and import new functionality to synthetic devices. Such devices inspired by natural systems could, in turn, play a crucial role in allowing biologists to explore the effects of physical transport and extreme conditions of temperature and pH on reaction systems. For example, engineered reaction containers can be physically and chemically defined to control the flux of molecules of different sizes and charge. The invention relates to a method for constructing small volume reaction containers through a combination of etching and deposition. The method allows for the fabrication of multiple devices that possess features on multiple length scales, specifically small volume containers with controlled porosity on the nanoscale. The invention further relates to the use of the small volume reaction containers in sensing (e.g., the container includes a biological sensing element of a biosensor) and the production or conversion of biological materials (e.g., enzymatic reactions, protein synthesis).

In one version of the present invention, multi-scale lithography and cryogenic deep reactive ion etching techniques are used to create ensembles of nanoporous, picoliter scale volume, reaction vessels within a microfluidic system. The invention provides for fabrication of these vessels and the process of the invention can be used to tailor vessel porosity by controlling the width of slits that constitute the vessel pores. Among other things, control of pore size allows the containment of nucleic acids and enzymes that are the foundation of biochemical reaction systems, while allowing smaller reaction constituents to traverse the container membrane and continuously supply the reaction.

In one aspect, the invention provides a structure for controlling transport of a material. The structure includes a side wall and an end wall at least partially defining a first volume and a second volume. The side wall separates the first volume and the second volume. The side wall includes one or more pores extending from a first surface facing the first volume to a second surface facing the second volume thereby providing a transport path between the first volume and the second volume. Each pore can have a limiting aperture in the range of 1 to 500 nanometers. Each pore can have a length of 5000 micrometers or less. The end wall and the side wall are monolithic being created by etching a substrate. The substrate can comprise silicon.

The structure can include a material located within the first volume or within the second volume. The material can have a physical or chemical property such that the material is selectively restricted by the pore or pores from passing from the first volume to the second volume or from passing from the second volume to the first volume. The material can be selected from nucleic acids, proteins, enzymes, metabolites, cell extract, and biological cells.

The structure can include means for controlling transport of the material both into and out of the first volume. The means for controlling transport of the material can comprise a physical or chemical coating on an inner surface of the pore. The coating can change volume upon application of a signal to the coating. The signal can be chemical, biological, electrical or optical.

In one form, the side wall has a thickness in the range of 0.5 to 5 micrometers. In one form, the limiting aperture is in the range of 1 to 200 nanometers. The side wall can have a shape selected from polygonal, circular, elliptical or oval. In one form, the side wall has a circular shape and has an inside diameter in the range of 1 to 100 micrometers.

The structure can include a second end wall in contact with the side wall, wherein the second end wall further defines the first volume and the second volume, and the second end wall can comprise a cover that comprises a silicone. The structure can include a second side wall further defining the first volume to form a channel structure. The structure can include a third side wall further defining the second volume to form a channel structure.

In one form, the side wall includes a first end and a second end, and a length from the first end to the second end ranges from 10 to 100 micrometers. The pore or pores can comprise a generally rectangular slit.

In the structure, the first volume may contain a first material, and the second volume may contain a second material reactive with the first material, and at least one of the first material and the second material can diffuse through the pore or pores.

In another aspect, the invention provides a microfluidic device including the structure for controlling transport of a material wherein a microchannel is formed in a surface of the substrate of the structure, and the microchannel defines the second volume of the structure. In one form, the side wall of the structure is arranged within the microchannel.

In yet another aspect, the invention provides a method for manufacturing volume defined regions. The method uses a substrate having an upper surface. A first etch mask is formed on the upper surface of the substrate. The first etch mask defines a side wall to be formed in the substrate, and the first etch mask further defines a limiting aperture to be formed in the side wall. A second etch mask is formed on the upper surface of the substrate. The second etch mask defines an end wall to be formed in the substrate. The substrate is etched to create the side wall, the limiting aperture and the end wall wherein the side wall and the end wall partially define a first volume and a second volume.

The first etch mask can be formed using electron beam lithography and a metal lift-off process, and the substrate can be cryogenically etched. The first etch mask can be formed with unmasked regions that define a plurality of limiting apertures to be formed in the side wall. The unmasked regions can be dimensioned to have a width in the range of 1 to 500 nanometers. The side wall can have a thickness in the range of 0.1 to 5 micrometers.

In still another aspect, the invention provides a method for reacting a first material and a second material. The method uses a structure for controlling transport of the first material and the second material. The structure includes a side wall and an end wall at least partially defining a first volume and a second volume. The side wall separates the first volume and the second volume. The side wall includes one or more pores extending from a first surface facing the first volume to a second surface facing the second volume thereby providing a transport path for the second material between the first volume and the second volume. Each pore can have a limiting aperture in the range of 1 to 500 nanometers. Each pore can have a length of 5000 micrometers or less. The end wall and the side wall are monolithic being created by etching a substrate. The first volume contains the first material and the second volume contains the second material. The second material is allowed to flow through the pore such that the second material reacts with the first material.

In this method, the second volume can be at least partially defined by a microchannel, and the second material can flow through the microchannel before transporting through the pore. The second material can react with the first material in a reaction controlled by a flux of the second material through the pore. In one version of the method, the first volume is less than 1 nanoliter.

In one version of the method, the second material reacts with the first material to produce a protein. In another version of the method, the second material reacts with the first material in an enzymatic reaction. In another version of the method, the first material or the second material comprises a biological sensing element of a biosensor.

In one non-limiting example of the invention, a 5.4 kb DNA plasmid was retained within the reaction vessels and labeled under microfluidic control with ethidium bromide. In another non-limiting example of the invention, a coupled enzyme reaction, in which glucose oxidase (GOX) and horseradish peroxidase (HRP) were contained and fed with a substrate solution of glucose and Amplex® Red (a colorless substrate that reacts with hydrogen peroxide with a 1:1 stoichiometry to produce highly fluorescent resorufin), was carried out under microfluidic control and monitored using fluorescent microscopy.

The fabrication techniques of the present invention are broadly applicable and can be adapted to produce devices in which a variety of high aspect ratio, nanoporous silicon structures can be integrated within a microfluidic network. The devices of the invention are amenable to being scaled in number and organized to implement more complex reaction systems for applications in sensing and actuation, material production or conversion, as well as fundamental studies of biological reaction systems.

These and other features, aspects, and advantages of the present invention will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
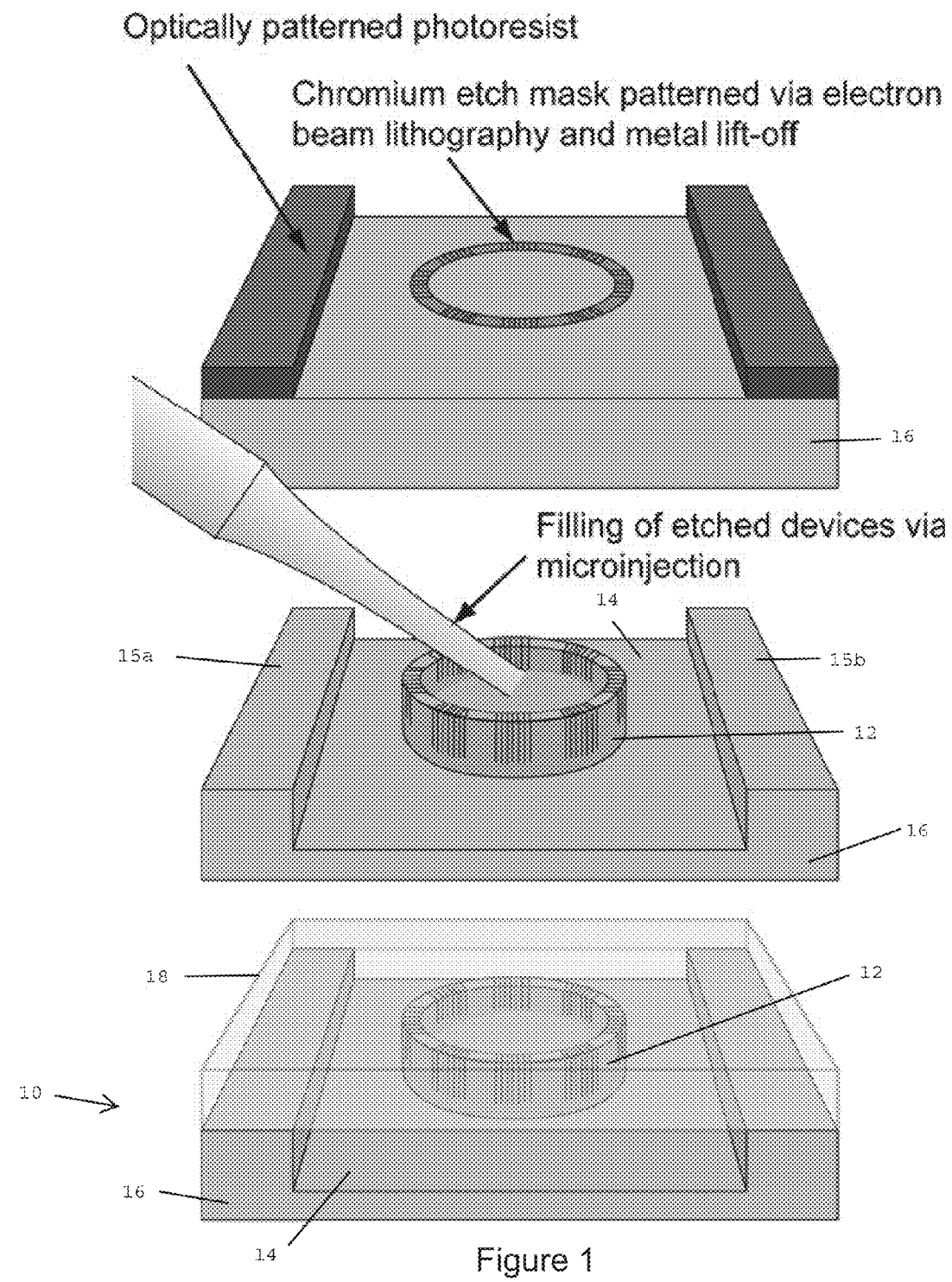
FIG. 1 shows that a fabrication of a structure in accordance with the invention of a nanoporous reaction vessel within a microfluidic channel between side walls is carried out by combining electron beam lithography and metal lift-off techniques with contact photolithography to define the reaction vessel and channel geometry in a silicon substrate (top). The pattern is transferred into the exposed silicon using cryogenic silicon etching and individual vessels are filled with reactants via microinjection (middle). Whole chips are then sealed with a silicone elastomer lid (bottom).

A combination of microfabrication and advanced lithographic techniques was used to create ensembles of nanoporous, picoliter volume, reaction vessels that are integrated within a microfluidic system in accordance with the invention in order to develop a cellular-scale reaction container that can be spatially addressed for monitoring and filling, while allowing both the storage and exchange of chemical information across the reactor membrane. The nanoscale pores or slits allow the exchange of molecular species (nutrients, signaling molecules, etc.) with the external environment or adjacent bioreactors.

In the invention, methods for refining pore size at a level that allows the differentiation between large and small molecules are achieved. The reaction vessels of the invention can be batch fabricated, allowing over a thousand identical containers to be produced in a single fabrication run, and can be stored indefinitely. Each of the reaction containers can be individually filled with the same or different reagents. Because the process used to fabricate the devices combines direct write electron beam lithography to define individual reaction volumes, the physical spacing of the containers and their individual properties, including total volume, pore size and shape, can be tailored for specific applications. For example, placing reaction vessels proximal to one another within a microfluidic channel, that contains only aqueous solution, can allow for reaction products to be exchanged between vessels via diffusion across membranes and convection along the microchannel. This can enable the study of reaction networks where the product of one reaction regulates or initiates a second reaction occurring downstream. The level of communication between vessels can be tailored for specific applications by controlling the proximity and porosity of containers, their positions relative to the direction of fluid flow, and the overall rate of fluid flow within the microchannel.

In one aspect, the invention provides a structure for controlling transport of a material. The structure includes a reaction vessel including a side wall defining an interior space of the reaction vessel. The reaction vessel and the pore are created by etching a substrate (e.g., silicon) as in the method of the invention. The side wall of the reaction vessel can have a shape selected from polygonal, circular, elliptical and oval. A transverse cross-section of the side wall of the reaction vessel can have a generally rectangular shape. More than one pore may be provided in the side wall of the reaction vessel, and each pore may have the same or different dimensions (i.e., the pores do not need to be identical).

The reaction vessel can be dimensioned such that each imaginary reference line having endpoints on opposite sides of an outer perimeter of the side wall of the reaction vessel has a length of 200 micrometers or less, more preferably 150 micrometers or less, more preferably 100 micrometers or less, more preferably 50 micrometers or less and more preferably 10 micrometers or less. For example, when the reaction vessel is circular, each reference line is an outside diameter that is equal to or less than the dimensions noted. When the reaction vessel is elliptical, the reference line with the maximum dimension will be the major axis, which will be equal to or less than the dimensions noted. The reaction vessel can have an inside diameter in the range of 1 to 100 micrometers, and more preferably 10 to 50 micrometers.

The side wall of the reaction vessel includes one or more pores extending from an outer surface to an inner surface of the side wall of the reaction vessel thereby providing a transport path between the interior space of the reaction vessel and a region outside of the reaction vessel. The pore or pores have a limiting aperture in the range of 1 to 500 nanometers, more preferably 10 to 400 nanometers, more preferably 20 to 300 nanometers, more preferably 30 to 200 nanometers, and more preferably 5 to 50 nanometers. In one form, the pore comprises a generally rectangular slit having a width, before modification with deposition processes, in the range of 20 to 200 nanometers.

The side wall of the reaction vessel can have a thickness in the range of 0.1 to 10 micrometers, more preferably 0.5 to 5 micrometers, and more preferably 1 to 2 micrometers. The side wall of the reaction vessel includes a top end and a bottom end, and the side wall of the reaction vessel can have a length from the top end to the bottom end in the range of 1 to 100 micrometers, preferably 10 to 50 micrometers, and more preferably 2 to 20 micrometers.

The pore or pores can have a depth extending from a top end of the side wall of the reaction vessel toward the bottom end. The depth of the pore or pores can extend from the top end of the side wall of the reaction vessel to a position on the side wall intermediate the top end and the bottom end. In one form, the depth of the pore or pores ranges up to 10 micrometers. In another form, the depth of the pore or pores ranges up to 20 micrometers. In another form, the depth of the pore or pores extends more than 50% of the way down from the top end to the bottom end of the wall.

A material can be located within the interior space of the reaction vessel or in the region outside of the reaction vessel. The material can have a physical or chemical property such that the material is selectively restricted by the pore or pores from passing from the interior space of the reaction vessel to the region outside of the reaction vessel or from passing from the region outside of the reaction vessel to the interior space of the reaction vessel. Non-limiting example materials include nucleic acids, lipids, proteins, carbohydrates, enzymes, and biological cells.

The structure for controlling transport includes means for controlling transport of the material both into and out of the interior space of the reaction vessel. The means for controlling transport of the material both into and out of the reaction vessel can be an arrangement of pores with interpore spacing. The means for controlling transport of the material both into and out of the reaction vessel can be a physical or chemical coating on an inner surface of the pore or pores. The coating can be selectively placed within a pore or selective pores can be differentially coated. The means for controlling transport of the material both into and out of the reaction vessel can be a coating on an inner surface of the pore or pores that changes volume upon application of a signal to the coating. The signal can be chemical, electrical or optical. The reaction vessel can have a layer of an oxide below the coating. The coating can change volume upon application of an electrical potential. In this non-limiting example, the coating comprises an electro-generated polymeric coating such as a conducting polymer selected from the group consisting of polypyrroles, polyanilines, polyacetylenes, polyindoles and polythiophenes. The coating can change volume upon sensing a change in pH. In this non-limiting example, the coating comprises an acrylic polymer.

In another aspect, the invention provides a microfluidic device. The microfluidic device includes a substrate having an upper surface. A microchannel is formed in the upper surface of the substrate. The microchannel has a width of 10,000 micrometers or less, more preferably 3000 micrometers or less, more preferably 500 micrometers or less, more preferably 300 micrometers or less, more preferably 200 micrometers or less. Preferably, the microchannel has a depth in the range of 1 to 100 micrometers, preferably 10-50 micrometers.

One or more reaction vessels are arranged in the microchannel. The reaction vessel includes a side wall defining an interior space of the reaction vessel. The side wall of the reaction vessel can be spaced inward from opposed side surfaces of the microchannel. The side wall of the reaction vessel include a pore extending from an outer surface to an inner surface of the side wall of the reaction vessel thereby providing a transport path between the microchannel and the interior space of the reaction vessel. The side wall of the reaction vessel includes one or more pores extending from an outer surface to an inner surface of the side wall of the reaction vessel thereby providing a transport path between the interior space of the reaction vessel and a region outside of the reaction vessel. The microchannel, the reaction vessel, and the pore can be created by etching the substrate, which is preferably silicon. The reaction vessel can have an outer layer of an oxide. Alternatively, molding or photopatterning of polymeric materials can be used. The microfluidic device can include a cover arranged over the substrate, the cover closing off the microchannel from above, wherein the side wall of the reaction vessel extends from a bottom surface of the microchannel to a bottom surface of the cover. The cover can be porous. The cover can also create the channel. Additional microchannels can be formed in the upper surface of the substrate with each additional microchannel including one or more reaction vessels arranged in each additional microchannel.

The pore or pores have a limiting aperture (transverse to the longitudinal pore length) in the range of 1 to 500 nanometers, more preferably 10 to 400 nanometers, more preferably 20 to 300 nanometers, and more preferably 30 to 200 nanometers. In one form, the pore comprises a generally rectangular slit (viewed in transverse cross-section) having a limiting aperture with a width in the range of 20 to 200 nanometers. Other pore cross-sectional shapes are possible. For example, pore walls with rounded or triangular edges will yield a limiting aperture of the shortest length.

The side wall of the reaction vessel can have a thickness in the range of 0.1 to 5 micrometers, and more preferably 1 to 2 micrometers. The side wall of the reaction vessel includes a top end and a bottom end, and the side wall of the reaction vessel can have a length from the top end to the bottom end in the range of 1 to 100 micrometers, and more preferably 10 to 50 micrometers.

The pore or pores can have a depth extending from a top end of the side wall of the reaction vessel toward the bottom end. The depth of the pore or pores can extend from the top end of the side wall of the reaction vessel to a position on the side wall intermediate the top end and the bottom end. In one form, the depth of the pore or pores ranges up to 10 micrometers.

The side wall of the reaction vessel can have a shape selected from polygonal, circular, elliptical and oval. In one form, the side wall of the reaction vessel has a circular shape. Preferably, the reaction vessel has an inside diameter in the range of 10 to 100 micrometers. In one form, the interior space of the reaction vessel has a volume in the range of 1 to 50 picoliters and more preferably 10 to 30 picoliters. In another form, the interior space of the reaction vessel has a volume in the range of 1 to 1000 picoliters, more preferably 1 to 500 picoliters, and more preferably 1 to 100 picoliters.

When a plurality of pores are present in the side wall of the reaction vessel, the plurality of pores can be arranged to have an interpore spacing of 50-5000 nanometers, and more preferably 1000-3000 nanometers. The plurality of pores can be arranged in sets of pores, the sets being spaced at intervals on the side wall of the reaction vessel. Each pore may have the same or different dimensions (i.e., the pores do not need to be identical).

The microfluidic device can include an inlet port in fluid communication with a first end section of the microchannel, and an outlet port in fluid communication with a second end section of the microchannel for transporting a fluid in the microchannel. The microchannel can contain a first material, and the reaction vessel can contain a second material reactive with the first material, and at least one of the first material and the second material can diffuse through the pore.

In yet another aspect, the invention provides a method for manufacturing a reaction vessel. In the method, a substrate having an upper surface is used. A first etch mask is formed on the upper surface of the substrate. The first etch mask defines an outer perimeter of a wall of a reaction vessel to be formed in the substrate by a subsequent etching step. The first etch mask further defines a perimeter of an interior space of the reaction vessel to be formed in the substrate by a subsequent etching step. The interior space is defined by the wall of the reaction vessel formed by a subsequent etching step.

The first etch mask can be formed using electron beam lithography and a metal lift-off process. Silicon wafers are spin-coated with electron beam resist and an electron beam lithography system is used to expose areas on the resist. Chromium or other etch compatible metals can then be deposited via electron beam evaporation. After soaking in a solvent, a chromium etch mask is left behind in the areas exposed by the electron beam. As an alternative, positive tone electron beam resist can be directly exposed, developed and used as an alternative, electron beam lithographically defined etch mask.

A second etch mask is formed on the upper surface of the substrate. The second etch mask defines a perimeter of a well formed by a subsequent etching step. The perimeter of the well is spaced outward from the outer perimeter of the wall of the reaction vessel formed by a subsequent etching step. The second etch mask can be formed using an optical lithography process.

After forming the first etch mask and the second etch mask, the substrate is etched to create the well in the upper surface of the substrate and to create the reaction vessel including the side wall defining the interior space of the reaction vessel. The reaction vessel is located in the well after the etching.

In one version of the method, the first etch mask is formed on the upper surface of the substrate such that the first etch mask includes an unmasked region extending from the outer perimeter of the wall of the reaction vessel to be formed in the substrate to the perimeter of the interior space of the reaction vessel to be formed in the substrate. Upon etching the substrate, a pore is created in the wall of the reaction vessel, and the pore provides a transport path between the well and the interior space of the reaction vessel. The first etch mask can be formed on the upper surface of the substrate such that the first etch mask includes a plurality of unmasked regions extending from the outer perimeter of the wall of the reaction vessel to be formed in the substrate to the perimeter of the interior space of the reaction vessel to be formed in the substrate. Upon etching, this creates a plurality of pores in the wall of the reaction vessel wherein each pore provides a transport path between the well and the interior space of the reaction vessel. The unmasked regions can be arranged in sets spaced at intervals on the wall of the reaction vessel to be formed in the substrate. The unmasked regions can be dimensioned to have a limiting aperture with a width in the range of 1 to 500 nanometers, more preferably 10 to 400 nanometers, more preferably 20 to 300 nanometers, and more preferably 30 to 200 nanometers.

In another version of the method, the second etch mask is formed such that the perimeter of the well defines a microchannel dimensioned to have a width of 20,000 micrometers or less, more preferably 10,000 micrometers or less, more preferably 5,000 micrometers or less, more preferably 3,000 micrometers or less, more preferably 1000 micrometers or less, more preferably 500 micrometers or less, more preferably 300 micrometers or less, more preferably 200 micrometers or less, and more preferably 100 micrometers or less.

In another version of the method, the first etch mask is formed on the upper surface of the substrate such that a thickness between the perimeter of the wall of the reaction vessel to be formed in the substrate and the perimeter of the interior space of the reaction vessel ranges from 0.1 to 5 micrometers, preferably from 0.5 to 5 micrometers, and more preferably 1 to 2 micrometers.

The substrate, which is preferably silicon, can be etched anisotropically via reactive ion etching or inductively coupled plasma reactive etching. In one version, the substrate, can be etched anisotropically using cryogenic inductively coupled plasma reactive ion etching. In one version of cryogenic etching, the silicon substrate is etched by exposing the substrate to a plasma of $SF_6$ and $O_2$ at temperatures of about −100° C. to −120° C. Anisotropic silicon etching can be realized as passivation of the side walls of the reaction vessel occurs during etching. This can create a reaction vessel wherein all transverse cross-sections of the side wall of the reaction vessel have a generally rectangular shape. This provides for precise volume control of the reaction vessel formed.

One version of the method comprises cryogenically etching the substrate to a depth below the upper surface of the substrate of up to 100 micrometers and preferably 1-50 micrometers. In one version of the method, the substrate is etched for a time period such that the interior space of the reaction vessel has a volume in the range of 1 femtoliter to 100 picoliters, preferably 1 to 50 picoliters, preferably 10-30 picoliters. An oxide, such as silicon dioxide, can be deposited on the etched substrate. Optionally, a coating can be deposited on an inner surface of the pore wherein the coating comprising a material that changes volume upon application of a chemical, electrical, biological, or optical signal to the coating. The coating on the inner surface of the pore can be biological, chemical or physical or a combination thereof. The coating on the inner surface of the pore can be an oxide, a polymer, a metal, or a combination thereof.

In still another aspect, the invention provides a structure for controlling transport of a material. The structure includes a reaction vessel including a side wall defining an interior space of the reaction vessel. The reaction vessel can be dimensioned such that at least a portion of the reaction vessel has a width of 3000 micrometers or less. The side wall of the reaction vessel includes one or more pores extending from an outer surface to an inner surface of the side wall of the reaction vessel thereby providing a transport path between the interior space of the reaction vessel and a region outside of the reaction vessel. The pore can have a limiting aperture in the range of 1 to 500 nanometers. The reaction vessel and the pore are created by etching a substrate.

A material can be located within the interior space of the reaction vessel or in the region outside of the reaction vessel. The material has a physical or chemical property such that the material is selectively restricted by the pore from passing from the interior space of the reaction vessel to the region outside of the reaction vessel or from passing from the region outside of the reaction vessel to the interior space of the reaction vessel.

The structure can include means for controlling transport of the material both into and out of the interior space of the reaction vessel. The means for controlling transport of the material both into and out of the reaction vessel can be a coating on an inner surface of the pore that changes volume upon application of a signal to the coating. The signal can be chemical, electrical, biological, or optical.

In one form, a section of the side wall of the reaction vessel has a thickness in the range of 0.5 to 5 micrometers, and the pore is located in the section of the side wall. The section of the side wall of the reaction vessel can include a top end and a bottom end, and the pore can have a depth extending from the top end of the section of the side wall of the reaction vessel. In one form, the pore can have a depth extending from the top end of the section of the side wall of the reaction vessel to a position on the section of the side wall intermediate the top end and the bottom end. The section of the side wall of the reaction vessel includes a top end and a bottom end, and a length from the top end to the bottom end can range from 10 to 100 micrometers. A transverse cross-section of the section of the side wall of the reaction vessel can have a generally rectangular shape. In one form, the pore comprises a generally rectangular slit having a limiting aperture with a width in the range of 20 to 200 nanometers.

In yet another aspect, the invention provides a structure for controlling transport of a material. The structure includes a first vessel having a width of 3000 micrometers or less, The first vessel has a first side wall. The structure includes a second vessel having a width of 3000 micrometers or less, and the second vessel has a second side wall. The structure includes a third wall common to the first vessel and the second vessel. The first side wall and the third wall define an interior space of the first vessel, and the second side wall and the third wall define an interior space of the second vessel. The third wall includes one or more pores extending from the first vessel to the second vessel thereby providing a transport path between the interior space of the first vessel and the interior space of the second vessel. The pore has a limiting aperture with a width in the range of 1 to 500 nanometers. The first vessel, the second vessel, the third wall, and the pore are created by etching a substrate.

A material can be located within the interior space of the first vessel or within the interior space of the second vessel. The material can have a physical or chemical property such that the material is selectively restricted by the pore from passing from the interior space of the first vessel to the interior space of the second vessel or from passing from the interior space of the second vessel to the interior space of the first vessel.

The structure can include means for controlling transport of the material between both interior space of the first vessel and the interior space of the second vessel. The means for controlling transport of the material comprises a coating on an inner surface of the pore that changes volume upon application of a signal to the coating. The signal can be chemical, electrical, biological or optical.

In one form of the structure, the third wall has a thickness in the range of 0.5 to 5 micrometers, and the pore is located in the third wall. The third wall includes a top end and a bottom end, and the pore has a depth extending from the top end of the third wall. In one form, the pore has a depth extending from the top end of the third wall to a position on the third wall intermediate the top end and the bottom end. The third wall includes a top end and a bottom end, and a length from the top end to the bottom end ranges from 10 to 100 micrometers. A transverse cross-section of the third wall can have a generally rectangular shape. The pore can have a generally rectangular transverse cross section, or space, having a limiting aperture with a width in the range of 20 to 200 nanometers.

In still another aspect, the invention provides a microfluidic device comprising a substrate having an upper surface, a microchannel formed in the upper surface of the substrate, and a membrane arranged in the microchannel. The microchannel can have a width of 1000 micrometers or less. The membrane can have a wall including a pore extending from a first surface to an opposite second surface of the wall thereby providing a transport path between a first section of the microchannel and a second section of the microchannel. The pore can have a limiting aperture with a width in the range of 10 to 500 nanometers. The membrane can have a plurality of pores. The microchannel, the membrane, the wall, and the pore can be created by etching the substrate. The substrate and the wall can comprise monolithic silicon.

The microfluidic device can include a cover arranged over the substrate wherein the cover closes off the microchannel from above, and wherein the wall of the membrane extends from a bottom surface of the microchannel to a bottom surface of the cover. In one form, an inlet port is in fluid communication with a first end section of the microchannel, and an outlet port is in fluid communication with a second end section of the microchannel.

In the microfluidic device, the microchannel can have a depth in the range of 10 to 100 micrometers and a width in the range of 50 to 150 micrometers. The wall can have a thickness in the range of 0.1 to 5 micrometers. The wall includes a top end and a bottom end, and the pore can have a depth extending from a top end of the wall. In one form, the pore has a depth extending from a top end of the wall to a position on the side wall intermediate the top end and the bottom end. The depth of the pore can range up to 20 micrometers. The pore can be a generally rectangular slit having a limiting aperture with a width in the range of 10 to 500 nanometers. The wall can include a plurality of pores, wherein each of the pores provides a transport path between the first section of the microchannel and the second section of the microchannel. Each of the pores can have a limiting aperture with a width in the range of 10 to 500 nanometers. The plurality of pores can be arranged to have an interpore spacing of 500-5000 nanometers.

In yet another aspect, the invention provides a method for manufacturing a microfluidic device. In the method, a first etch mask is formed on an upper surface of a substrate such that the first etch mask defines opposed outer surfaces of a wall of a membrane to be formed in the substrate. A second etch mask is formed on the upper surface of the substrate such that the second etch mask defines a perimeter of a well to be formed in the substrate. The second etch mask is dimensioned such that the first etch mask extends between opposite sides of the perimeter of the well to be formed in the substrate. The substrate is etched to create the well in the upper surface of the substrate and to create the membrane including the wall. In one form, the substrate is silicon.

In one version of the method, the first etch mask is formed on the upper surface of the substrate such that the first etch mask includes an unmasked region extending between the opposed outer surfaces of the wall to be formed in the substrate, and the substrate is etched to create a pore in the wall of the membrane, wherein the pore provides a transport path between a first section of the well and a second section of the well.

In another version of the method, the first etch mask is formed on the upper surface of the substrate such that the first etch mask includes unmasked regions extending between the opposed outer surfaces of the wall to be formed in the substrate, and the substrate is etched to create a plurality of pores in the wall of the membrane, wherein the pores each provide a transport path between a first section of the well and a second section of the well.

The unmasked regions can be dimensioned to have a width in the range of 1 to 500 nanometers. The second etch mask can be formed such that the perimeter of the well defines a microchannel dimensioned to have a width of 3000 micrometers or less. The first etch mask can be formed on the upper surface of the substrate such that a thickness of the wall of the membrane to be formed in the substrate ranges from 0.1 to 5 micrometers.

In one version of the method, the first etch mask can be formed using electron beam lithography and a metal lift-off process. The substrate can be cryogenically etched using inductively coupled plasma reactive ion etching. The substrate can be etched to a depth below the upper surface of the substrate of up to 100 micrometers. The substrate can be anisotropically etched. A coating can be deposited on an inner surface of the pore.

Addition of materials to the pore can be achieved by various methods. Plasma enhanced chemical vapor deposition (PECVD) may be used to provide conformal coatings of oxides on the reaction vessel surfaces. PECVD silicon dioxide coating enables use of a broad spectrum of silane-based surface modification techniques that have been developed for derivatization of silica-based microfluidic and microcapillary platforms. These techniques provide highly controlled modification of surface charges and hydrophilicity of nanoscale structures of the present invention, as well as nanoscale manipulation of pore widths using both electrical- and pH-modulation of polymeric composites These conformal coatings can also be exploited to reduce the pore width. Atomic Layer Deposition (ALD) is an alternative deposition process that can be used to modify these structures. This allows a more controlled, conformal, coating to be deposited. These deposition methods can reduce the limiting aperture to 200 nanometers or less.

Chemical functionalization of the structures can be used to construct nanosensors and for enabling selective transport and actuation properties when functioning as a membrane structure. Chemical functionalization can provide the essential interface between the solution phase entities desired to detect and control. Therefore, chemical derivatization schemes that alter the chemical and physical properties of the pores of the reaction vessel be used.

Active or passive gating properties of the pores of the reaction vessel can be achieved. Controlled transport through the pores of the reaction vessel can serve two functions: (1) controlled presentation of an analyte to an interior sensing element in the reaction vessel or (2) controlled release of a material from the reaction vessel that results from an appropriate trigger (e.g., electrical, biological, chemical, optical).

Electrogenerated polymers, such as conducting polymers including polypyrrole, polyaniline, polyacetylene, polyindole and polythiophenes, can be used with the reaction vessel to create a microactuator that is electrically controllable. This is accomplished by incorporation of a large anion, such as dodecylbenzenesulfonate during the polymerization process. When a negative potential is applied, the polypyrrole is reduced and cations diffuse into the polymer. This results in a swelling of the polymer that is reversible upon oxidation of polypyrrole. This volume change is useful for actuation of devices and may also be useful for creating a valve structure in the pores of the reaction vessel. Upon actuation the "pore" size can be reduced or sealed. In the application of mechanical actuators, the volume change is proportional to the applied voltage. This feature may also be applicable for altering the pore size. Selective transport of ions can also be achieved with these polymer coatings.

The use of pH sensitive polymer matrices for actuation of membrane transport through the pores can also be used. PECVD oxide-coated pores can be modified using silane chemistries for the covalent attachment of pH-sensitive polymeric networks including n-alkyl acrylamides, and acrylimide/poly(propylacrylic) acid copolymers. These materials feature sharp, reversible, phase transitions at physiological conditions sensitive to both temperature and pH. In addition to providing controlled gating via polymer swelling and collapse of the pores of the reaction vessel, the pH-sensitive phase transition can also be used to store and release materials from the polymer itself.

Electrical addressing can also be exploited to generate electrical potential gradients on either side of the wall of the reaction vessel. Addressable electrodes, for example, in the form of gold pads or nanofibers, can be placed on either side of the wall of the reaction vessel. An electrical gradient can be generated to control the flux of charged species between the interior space of the reaction vessel and a region outside of the reaction vessel.

EXAMPLES

The following Examples have been presented in order to further illustrate the invention and are not intended to limit the invention in any way.

Example I

Non-limiting example fabrication techniques of the invention were used to create reaction containers and the impact of those techniques on pore size and functionality are described in Example I. In addition, the methods used to tailor the effective size of device pores and a demonstration of the ability to contain larger biomolecules (plasmid DNA, and enzymes) within the reaction containers while microfluidically addressing the reaction containers and exchanging small molecules are provided by the invention. Although two reactions are described in Example I (i.e. the labeling of DNA in the reaction vessel with ethidium bromide, and a coupled enzyme reaction of HRP and GOX with a fluorogenic substrate to determine glucose concentrations), the invention is not limited to these type of reactions. The long-term and overall stability, addressability, and ability to discretely tailor reaction vessel properties as a means of controlling material exchange suggest that the described platform of the invention represents an useful complementary alternative to bioreactors based on organic membrane systems.

A. Materials and Methods

1. Chemicals And Reagents

Fluorsbrite™ 100 nm and 350 nm latex beads used in size exclusion experiments were obtained from Polysciences Inc. (Warrington, Pa., USA). Amplex®

Red was purchased from Invitrogen. Ethidium bromide, horseradish peroxidase, glucose oxidase and other reagents were purchased from Sigma Aldrich. A Sylgard 184 Elastomer Kit was obtained from Fisher Scientific.

Plasmid DNA (5.4 kb) used in the DNA containment and labeling experiments was constructed by recombining a gene for enhanced GFP (eGFP) into pDEST17 (Invitrogen) to allow expression of 6×His-GFP from a T7 promoter. Plasmid DNA was purified from *Escherichia coli* BL21 (DE3) (Invitrogen) using a Qiagen Midiprep kit (Valencia, Calif., USA) according to manufacturer's instructions. Production of eGFP was carried out by using the plasmid described above to transform *E. coli* BL21 (DE3) cells.

IPTG was added to a final concentration of 1 mM to induce expression of 6×His-GFP. His-tagged protein was purified from cell lysates on a Ni-NTA column according to manufacturer's instructions (Qiagen, no. 31314). Protein concentration was determined using a Bradford assay (Pierce).

2. Nanoporous Reaction Vessel Fabrication

The fabrication of nanoporous reaction vessels is carried out using a combination of electron beam and optical lithography techniques to define the etch masks for the reaction vessels and surrounding microchannels. Electron beam lithography is used to define the etch mask for the reaction containers, and contact photolithography is used to align and define the microchannels. Once the etch masks are defined, the vessels and microchannels are etched simultaneously using a cryogenic silicon etching process. A brief plasma enhanced chemical vapor deposition (PECVD) process is used to coat the reaction vessel with silicon dioxide and to modify the final pore size.

FIG. 1 shows that a fabrication of a structure 10 in accordance with the invention of a nanoporous reaction vessel 12 within a microfluidic channel 14 between side walls 15a, 15b is carried out by combining electron beam lithography and metal lift-off techniques with contact photolithography to define the reaction vessel 12 and channel geometry in a silicon substrate 16 (top). The pattern is transferred into the exposed silicon using cryogenic silicon etching and individual vessels are filled with reactants via microinjection (middle). Whole chips are then sealed with a silicone elastomer lid 18 (bottom).

Figure 2:
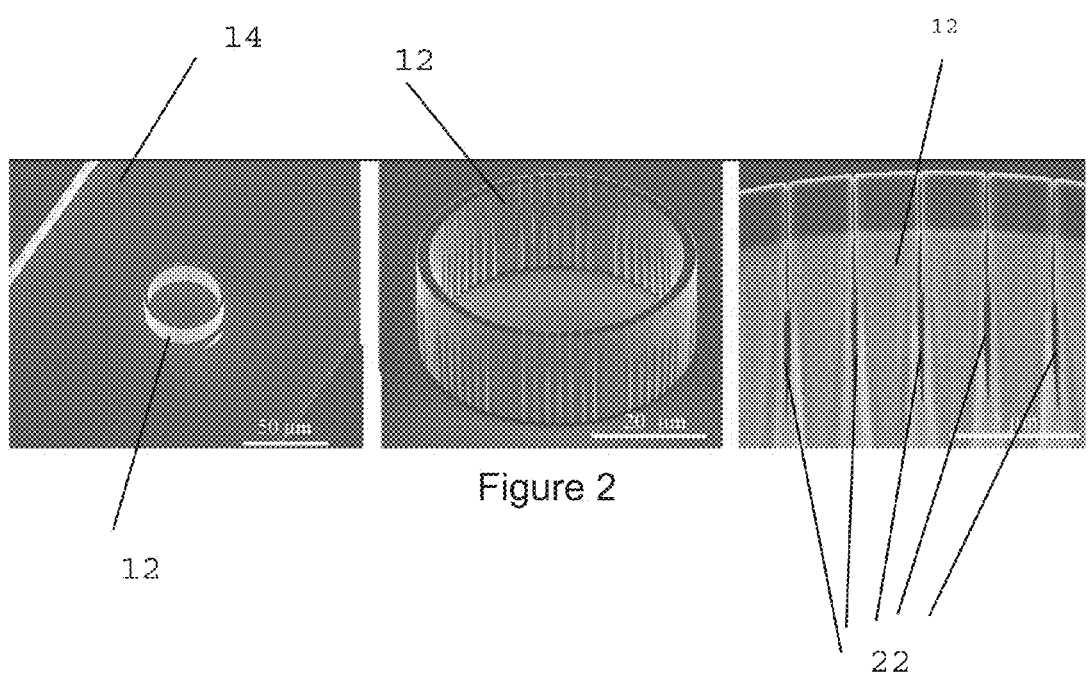
FIG. 2 shows scanning electron micrographs of reaction vessels according to the invention taken prior to filling and sealing showing the integration of porous vessels within a microfluidic channel (left), the overall device size and pore locations (center), and the nominal pore size (right). Images were taken at a 30° stage tilt.

FIG. 2 shows scanning electron micrographs of reaction vessels 12a to 12e according to the invention taken prior to filling and sealing showing the integration of porous vessels within a microfluidic channel (left), the overall device size and pore locations (center), and the nominal pore size (right). Images were taken at a 30° stage tilt.

Fabrication was carried out using standard 400 silicon wafers with a (100) crystal orientation. To define the etch mask for the reaction vessels, wafers were spin-coated with NANO™PMMA 495 A4 electron beam resist (Microchem Corp., Newton, Mass., USA) at 2500 rpm for 45 seconds and baked on a hotplate for 10 minutes at 180° C. A JEOL JBX9300-FS electron beam lithography system operating at 100 kV and 2 nA was used to expose the geometry of the reaction container and optical alignment marks for subsequent processing. The dose was approximately 1250 µC cm$^{-2}$, but was modulated through iterative exposure and examination via scanning electron microscopy to yield the desired pore sizes. Patterns were developed for 1 minute in 1:3 methyl isobutyl ketone (MIBK):isopropyl alcohol (IPA), rinsed with IPA, and dried with nitrogen. The patterns were then exposed to a brief oxygen plasma (10 sccm, 150 mT, 100 W, 6 s) before depositing 15 nanometers of chromium via electron beam evaporation. Samples were soaked in acetone, and rinsed with IPA and water, leaving behind a chromium etch mask in the areas exposed by the electron beam.

Microchannel masks were defined using conventional contact alignment optical lithography. A negative photoresist, JSR Micro NFR 016 D2 55 cp (JSR Micro Inc., Sunnyvale, Calif., USA) was chosen as the etch mask for the microchannels as it was more resistant to cracking during the cryogenic etching process. Resist was spin-coated at 6000 rpm following wafer treatment with Microprime P20 Adhesion promoter. Wafers were baked on a hotplate at 90° C. for 90 seconds, exposed, and baked for an additional 90 seconds at 90° C. Samples were then developed in CD26 (Microchem Corp., Newton, Mass., USA) (<5% tetramethylammonium hydroxide) for 20 seconds, until the microchannels were visibly developed. After rinsing and drying with $N_2$, samples were baked for 3 minutes at 180° C.

Once the chromium and photoresist etch masks were defined, samples were exposed to a brief oxygen plasma (10 sccm $O_2$, 150 mT, 400 W, 1 min) to remove any organic solvent and resist residue left on the exposed silicon. Samples were then etched in an Oxford Plasmalab 100 inductively coupled plasma reactive ion etching systems using a cryogenic silicon etching process. This process is carried out by exposing samples to a plasma of $SF_6$ and $O_2$ at −110° C. The oxygen flow rate and RF bias of the plasma are used to balance etching and sidewall passivation to allow highly anisotropic etching of the exposed silicon to yield high aspect ratio features in silicon. Reaction vessels and channels were etched to a depth of 15 µm at a rate of approximately 3 µm min$^{-1}$. Following the completion of etching, mask materials were removed by an exposure to a more aggressive oxygen plasma and brief soak in chromium etchant.

Following removal of the etch mask materials, an Oxford Plasmalab 100 plasma enhanced chemical vapor deposition system was used to deposit silicon dioxide on the structures. The duration of the deposition was varied to control final pore dimensions and tune size selectivity of the nanoporous reaction vessels.

3. Device Packaging and General Imaging Techniques

Polydimethylsiloxane (PDMS) used to seal the microchannels was mixed at a 10:1 w/w ratio, degassed and cured for approximately 1 hour at 70° C. PDMS was cut into 4 millimeter thick pieces matching the microfluidic chip size. Inlet and outlet holes were punched in the device using an 18-gauge blunt tip needle. 0.020" outside diameter polyethylene tubing was press fit into the PDMS. The packaged chip measured approximately 4 cm long by 15 mm wide. The number and type of individual reaction vessels can be modified from one chip to the next. Each chip configuration consisted of 30 vessels, three groups of five in each of two channels, spaced at equal intervals along the channel. Each group of five devices can be imaged simultaneously in the viewing area of a Zeiss Axioscope epifluorescent microscope with a 10× objective. For the experiments described here, each of the vessels was created with the same nominal pore size, a 200 nanometer wide pore that extended across the full width of the vessel wall. The ability to control pore size down to tens of nanometers via electron beam lithography, prior to coating with silicon dioxide, was demonstrated by the creation of test reaction vessels with 5 different size pores. Pore width was designed to be 30, 50, 80, 100, and 200 nanometers. The four smallest sizes started at 200 nm wide and tapered to a pore of width 30, 50, 80, or 100 nanometers and length of 600 nanometers.

4. Loading of Nanoporous Reaction Vessels

Prior to sealing with a PDMS "roof," chips were treated with a 1 mg mL$^{-1}$ solution of bovine serum albumin for 10 minutes to prevent nonspecific adsorption of reaction constituents to the device walls. Individual vessels were filled using an adapted cell microinjection system. A hydraulic manipulator with manual injection pump was attached to a Burleigh micromanipulator. Pulled micropipettes with tip diameters of two micrometers (Small Parts Inc., Logansport, Ind., USA) were backfilled with the desired reagent using a flexible polyimide needle (World Precision Instruments, Sarasota, Fla., USA). Chips were placed under a stereomicroscope and were manually filled by touching the filled pipette into the center of the reaction vessels. The volume of the device structure and viscosity of the filling solution dictated the amount of material injected, as materials generally wetted the device to the inner wall of the membrane, allowing repeatable filling of devices. For DNA experiments solutions contain 4% glycerol to reduce the risk of overfilling devices.

5. Functional Demonstration of Size Exclusion and Molecular Containment

To demonstrate the functional size range of the 200 nanometer pore devices, microchannels were loaded with solutions of 100 nm and 350 nm Fluorsbrite™ latex beads. Care was taken to insure that air bubbles were not trapped in the reaction vessels. DNA containment and labeling experiments were carried out by filling reaction vessels with concentrations of DNA ranging from 0.06 to 600 ng $\mu L^{-1}$ in buffer. A labeling solution of ethidium bromide (EtBr) at a concentration of 100 $\mu$g $mL^{-1}$ was injected into the microchannel. Images were captured before adding EtBr, immediately after adding EtBr, and after 30 minutes under flow at a flow rate of 10 $\mu L\ h^{-1}$.

6. Containment of Proteins and Coupled Enzyme Reactions

Flow experiments were conducted by first filling the reaction vessels with a 100 $\mu$g $mL^{-1}$ solution of GFP. Under a steady flow of 10 $\mu L\ h^{-1}$ ensembles of reaction vessels were imaged. A Retiga firewire camera and QCapture software were used to capture fluorescent and bright field images. Care was taken to ensure that exposure times, binning and other relevant camera settings were maintained to allow reasonable comparisons to be made between experiments. A shutter was used to minimize photobleaching when images were not being captured.

Coupled enzyme reactions were carried out by first filling reaction vessels with a mixture of horseradish peroxidase (0.25 U $mL^{-1}$) and glucose oxidase (0.25 U $mL^{-1}$) in PBS buffer. Channels were filled with a solution containing 100 $\mu$M Amplex®Red and glucose ranging in concentrations from 100 $\mu$M to 100 mM. Fluorescent images were recorded at different time intervals under constant flow conditions.

B. Results and Discussion

1. Device Fabrication

The hybrid lithography techniques used in the reaction vessel fabrication, combining optical and electron beam lithography, provide for a robust and flexible process by which device geometries and configurations can be readily varied for different applications. The use of electron beam lithography to define the reaction vessel etch mask allows definition of features below 30 nanometers. Additionally, because the containers are defined using a direct write technology, the number, organization and physical attributes of the containers can be varied across samples and from run to run. Batch fabrication of samples allowed 8 chips to be completed per wafer. Electron beam lithography write times were relatively short, 45 minutes per wafer, allowing multiple samples to be produced in an afternoon. Further reductions in write times could be realized by using higher sensitivity electron beam resist, increasing the electron beam current and increasing the writing shot pitch. Completed vessels had an inner diameter of 40 micrometers, a 2 micron thick wall, and 56 pores (8 sets of 7 pores spaced at 45° intervals). Structures and channels were nominally 15 micrometers tall, with heights measured using physical profilometry. The internal volume of the structures was approximately 18 picoliters. A diameter of 40 micrometers was chosen because of the relative ease with which the devices could be imaged and filled using microinjection. FIG. 2 illustrates the multi-scale features of the completed devices.

Figure 3:
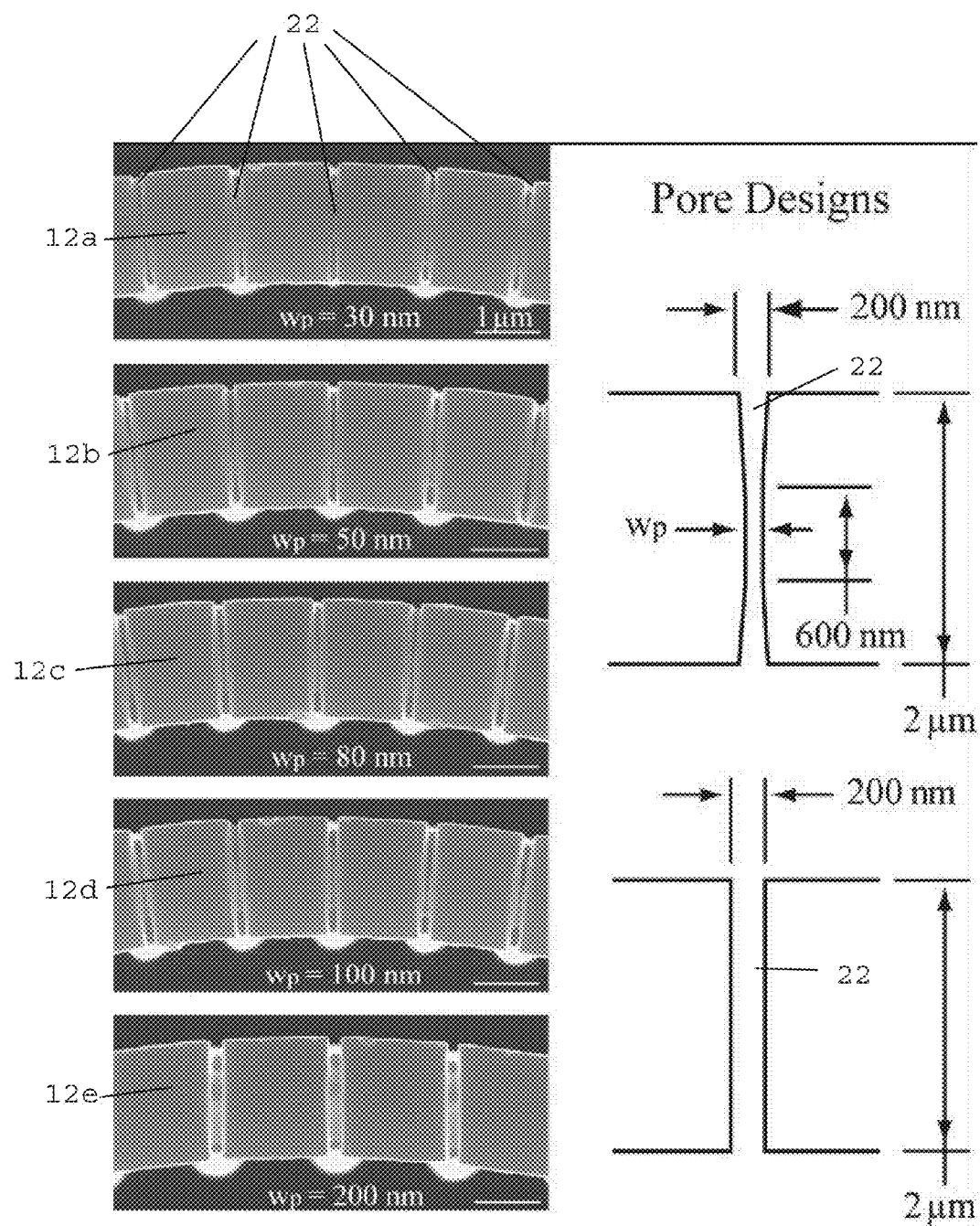
FIG. 3 shows top view scanning electron micrographs and drawings of the porous membranes of the invention taken at a magnification of 35 000× showing the different dimension pores achieved via electron beam lithography and cryogenic silicon etching. Pore width ($w_p$), corresponds to the dimension used in the lithography patterns. Final dimensions ranged from approximately 10 to 30 nanometers smaller than the CAD-defined pore width.

While electron beam lithography could be used to create pores 22 below 30 nanometers in reaction vessels 12 (see FIG. 3), we ultimately found that the modification of larger pores through silicon dioxide deposition was a more effective strategy for reducing and controlling pore size. Thus, the containment experiments of these Examples were performed with devices having initial pore widths of 200 nanometers and a minimal silicon dioxide coating (2 minutes duration). One of the primary drivers for making this choice is the coupling of slit width with etch depth as shown in FIG. 4.

Figure 4:
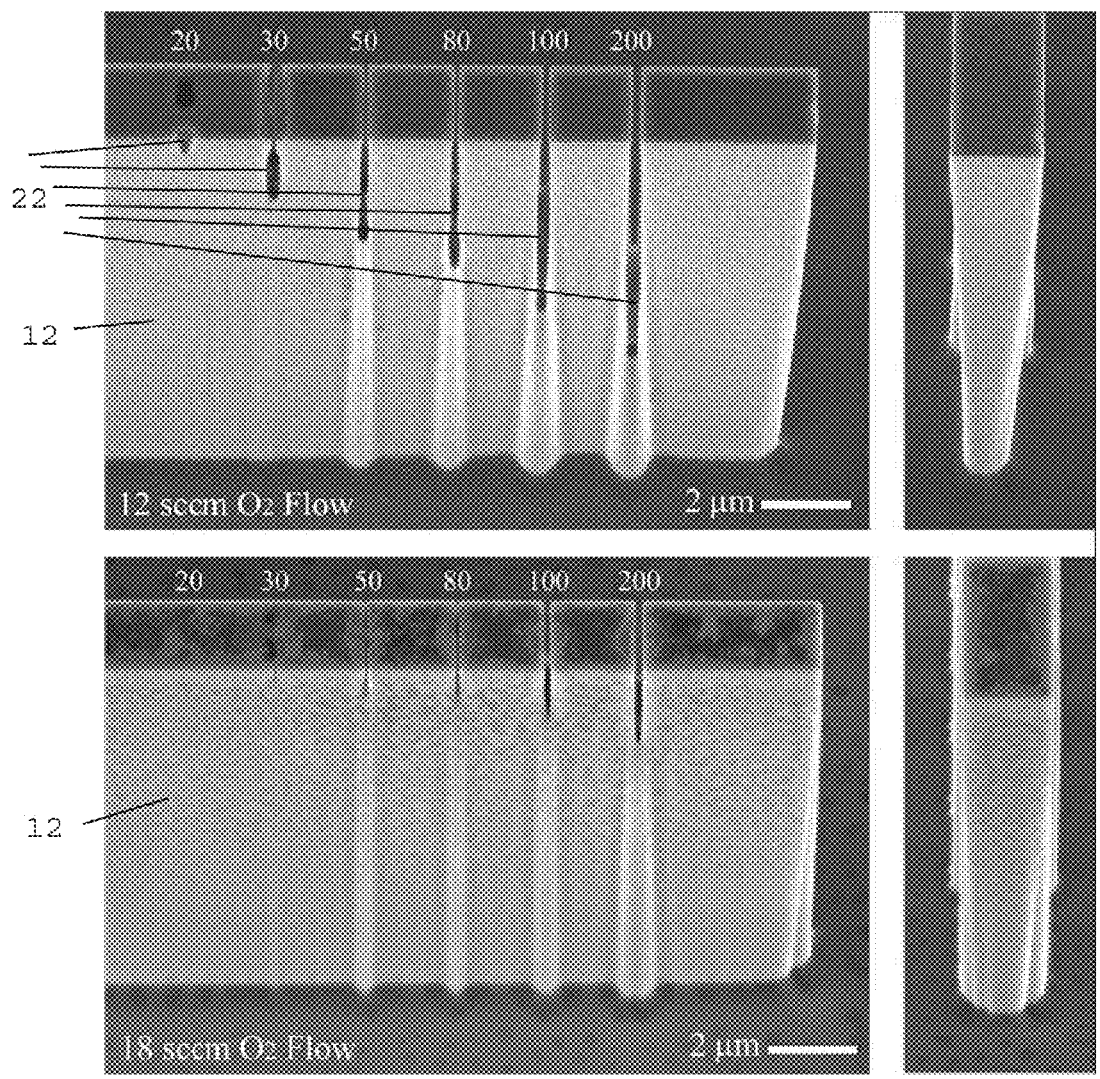
FIG. 4 shows membrane test structures of the invention with different sized pores (labeled in nm) that were used to examine the effects of pore width and oxygen flow rates on pore depth. At 12 standard cubic centimeters per minute (sccm) of oxygen flow (top) no passivating material is visible and 200 nanometer pores etch more than 60% of the membrane height. At higher oxygen flow rates (bottom), passivation is increased leaving passivating polymer deposited on structures and severe reductions in pore depth.

As can be seen in FIGS. 2 and 4, even though the pores 22 and the larger vessel structure 12 are etched simultaneously the overall depth of the device and channel is nearly twice the depth of the pore slit. This can be attributed to aspect ratio dependent etching resulting from poor diffusion of reactive gases and depletion of etching reactants within the narrower slits. Test structures combining different pore widths side by side were constructed to illustrate the effects of pore width on etch depth. In addition, the effects of plasma oxygen content on sidewall profile are illustrated (see FIG. 4). During the cryogenic etch process a silicon-oxy-fluorine polymer forms on the sidewalls of the structure while reactive fluorine ions etch exposed silicon. By balancing the lateral etch rate with the passivating polymer deposition an anisotropic etch process can be developed. At low oxygen content some undercutting can occur as shown in the 12 sccm $O_2$ flow condition (top of FIG. 4), while at higher oxygen content the deposition and presence of the passivating polymer become notable (bottom of FIG. 4). The sensitivity of the balance in passivation and etching is notable near the slits where a small pillar-like structure is noticeable beneath the pore. Without intending to be bound by theory, we hypothesize that this results from the local consumption of etching gases in the etching of the pore slit. Locally this results in an excess of passivating gases below the slit, resulting in local variations in sidewall profile and the appearance of the pillar-like structures below the slit. It is important to note, and indicated from FIG. 4, that the cryogenic etching process is sensitive to oxygen content. The choice of oxygen flow rate must therefore be fine-tuned for different structure designs and geometries. Etch profiles were also affected by variations in RF power, though the effects were less dramatic (not shown).

Thus, we have demonstrated direct fabrication of pores from 30-200 nanometers diameter prior to modification with silicon dioxide. Pores range in size from 1-50 nanometers following modification with silicon dioxide.

2. Functional Demonstration of Size Exclusion and Molecular Containment

Figure 5:
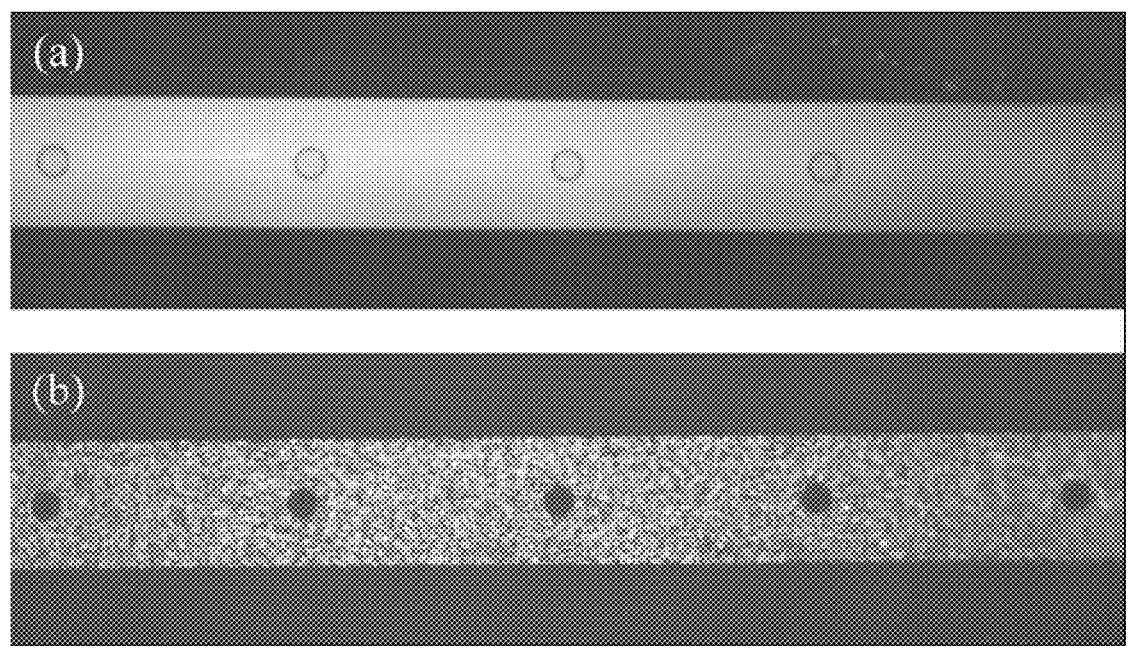
FIG. 5 shows that fluorescent polystyrene beads were introduced into microchannels at modest flow rates. In (a), 100 nm diameter beads traversed the reaction vessel membrane as expected, while larger (b) 350 nm beads were excluded.

In separate experiments, 100 and 350 nm beads were injected into microfluidic devices containing vessels with 200 nanometer pores. 100 nm beads easily entered the vessels while 350 nm beads were excluded. FIG. 5 demonstrates that vessels are defect free and have a functional pore size, and size distribution between 100 nanometers and 350 nanometers. In previous work we examined the use of patterned carbon nanofiber membranes for similar separations, but found that defect density resulting from the nanofiber growth resulted in "leaky" membrane structures. (See, Fowlkes, et al., Nanotechnology, 2008, 19; and Retterer, et al., Carbon, 2008, 46, 1378-1383.) In addition to being free of defects, the deterministic nature of the structures used here helps to make modeling and simulation of these systems more tractable. This basic demonstration helps illustrate the potential utility in using the reaction vessels to exclude molecules or functionalized particles based on size. Surface modification techniques may be used to create pores that enable selection based on charge or selective binding.

Figure 6:
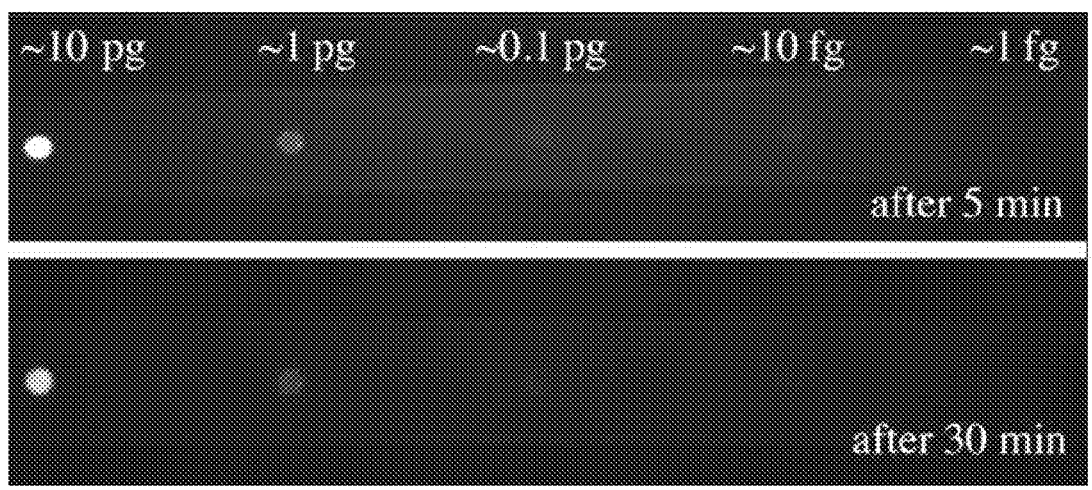
FIG. 6 shows that plasmid DNA was loaded into reaction vessels with a minimal silicon dioxide coating at different concentrations (600 ng $\mu L^{-1}$-0.06 ng $\mu L^{-1}$) corresponding to the total mass shown. Plasmid DNA was labeled in situ with ethidium bromide. Fluorescence was evident immediately and did not diminish, indicating that plasmid DNA is retained, and small molecules are able to traverse the membrane and react with the plasmid.

In DNA labeling experiments 600 ng $\mu L^{-1}$, 60 ng $\mu L^{-1}$, 6 ng $\mu L^{-1}$, and 0.6 ng $\mu L^{-1}$ and 0.06 ng $\mu L^{-1}$ of 5.4 kb plasmid DNA were loaded in reaction vessels using the Burleigh microinjection system. Images taken 30 minutes after ethidium bromide is introduced through the microfluidic channel illustrate a fluorescent response proportional to DNA concentration (see FIG. 6). Only limited degradation of the fluorescent signal was observed over time indicating that the DNA is contained within the reaction vessels over extended periods. The successful containment of DNA while allowing small molecules to traverse the reactor membrane and intercalate the DNA suggests a potential path for the development of more complex systems based on cell-free transcription and translation. DNA containment experiments were carried out in reaction vessels with a 200 nanometer pore and minimal silicon oxide coating.

Figure 7:
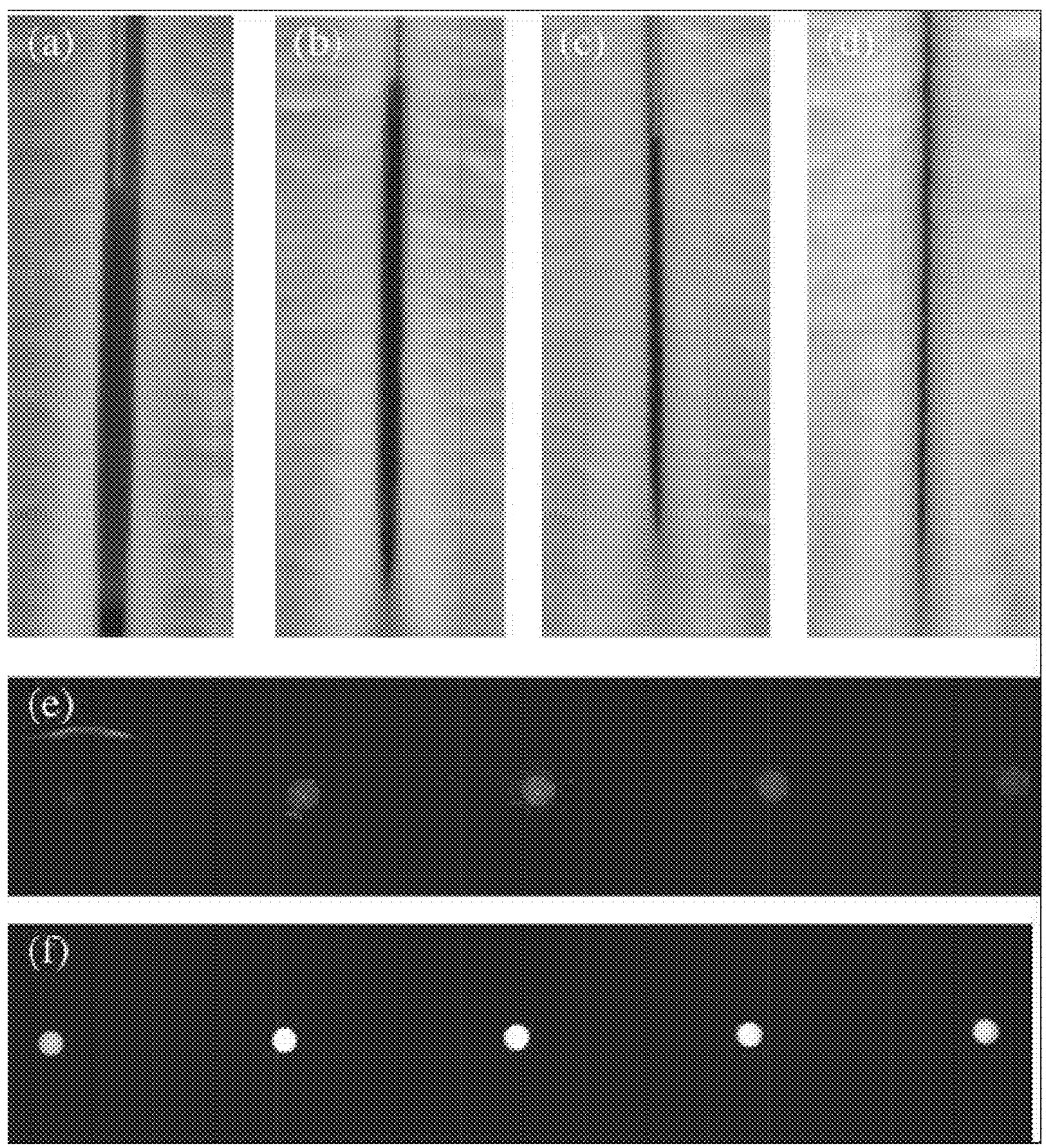
FIG. 7 shows that the deposition of silicon dioxide on membrane structures can be used to reduce pore width. At a deposition rate of approximately 60 nm $min^{-1}$ on flat horizontal surfaces, deposition on vertical, pore sidewalls is considerably less. Pores are shown after (a) 2, (b) 4, (c) 6, and (d) 8 minutes of plasma enhanced chemical vapor deposition (PECVD) silicon dioxide deposition. The retention of green fluorescent protein was observed after 5 minutes in reaction vessels coated with silicon dioxide for (e) 4 minutes (100 ms digital camera exposure) and (f) 6 minutes (50 ms digital camera exposure). Each of the devices shown was filled with the same concentration of GFP.

A 5.4 kb plasmid has an experimentally and computationally predicted radius of gyration between 80 and 240 nanometers. This suggests an overall diameter that fluctuates near the 200 nanometer pore slit width. Assuming a diffusion coefficient of approximately $3 \times 10^{-8}$ cm$^2$ s$^{-1}$ for the 5.4 kb plasmid, a simple numerical model of free leakage of DNA through the 200 nanometer pores approximates a 50% reduction in concentration in less than 3 minutes, and a near zero concentration within 10 minutes. The persistence of fluorescence from the labeled DNA after 30 minutes and the absence of fluorescent material outside of the vessels indicate that the plasmid is not able to freely diffuse through the reaction vessel membrane. Ultimately, to control the transport of specific proteins or small molecules across and between reaction vessels, the pore size and surface charge or functionality could be tuned further. Towards that end we examined the use of plasma enhanced chemical vapor deposition to reduce pore size (width) and limit the flux of GFP across the vessel membranes. A comparison of GFP retention within devices having different thickness coatings of silicon dioxide was carried out. Individual device chips were subjected to different duration PECVD silicon dioxide depositions. From the scanning electron micrographs shown in FIG. 7, it is clear that there is a considerable reduction in pore size as more silicon dioxide is deposited on the reaction vessels. Though it would be difficult to directly measure the effective gap size through the entire thickness of the membrane using imaging techniques, changes in the retention of GFP within devices that have different thickness silicon dioxide coatings suggest that we can modify pore size to tune the flux of small molecules across the reactor membrane and to contain proteins of a particular size (see FIG. 7).

3. Coupled Enzyme Reaction System

Figure 8:
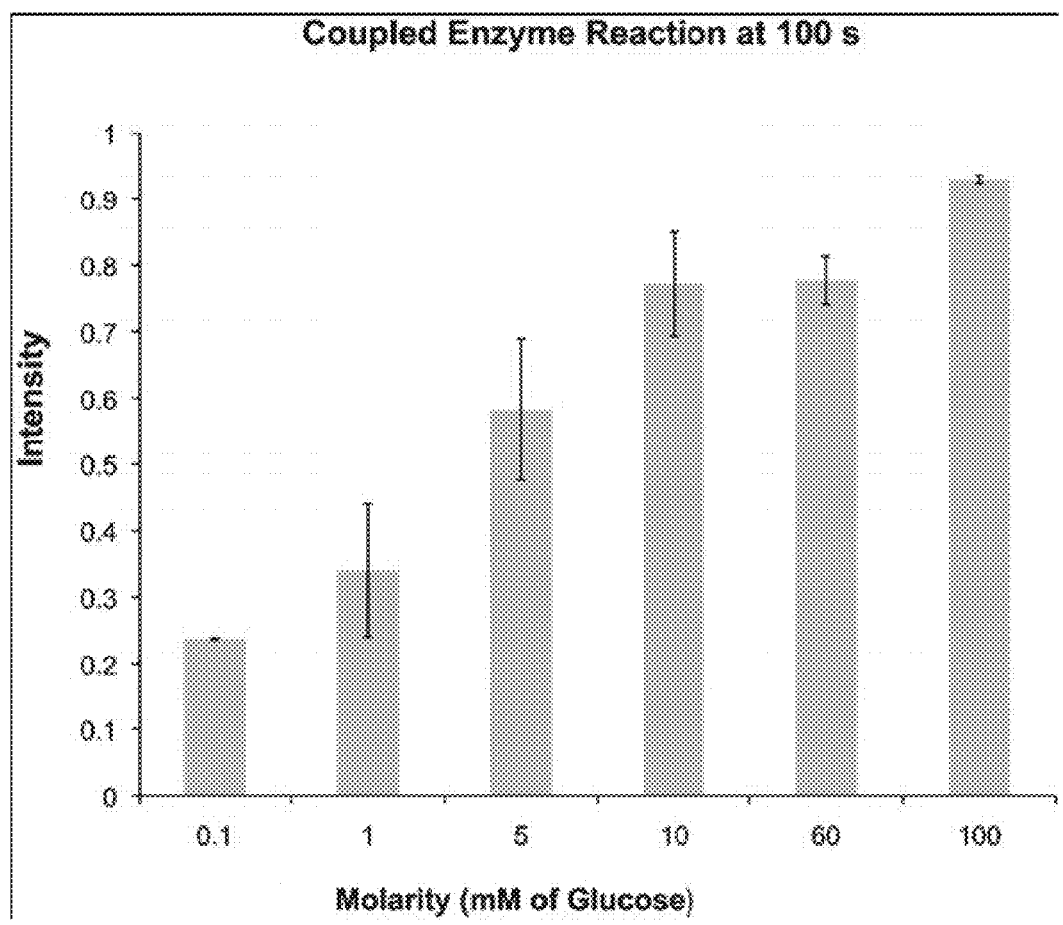
FIG. 8 shows fluorescence intensity resulting from a coupled GOX-HRP enzymatic conversion of glucose and Amplex® Red to fluorescent resorufin at a fixed time point of 100 seconds. GOX-HRP were loaded into reaction vessels at a concentration of 0.25 U $mL^{-1}$.

The ability to controllably contain macromolecules opens the possibility for applications in both sensing and the production or conversion of biological materials. Coupled enzyme reactions were carried out in vessels subjected to a 7 minute PECVD silicon dioxide coating. The retention of GOX and HRP within the reactors is demonstrated by the continued fluorescence of the coupled reaction system under steady flow. It is conceivable that nonspecific adsorption could account for some percentage of the retained fluorescence, but one would expect that this would manifest as some initial drop in fluorescence intensity followed by a longer steady state condition. We see a proportional response of fluorescence with glucose concentration 100 seconds after the addition of the substrate. FIG. 8 illustrates the measured fluorescence intensity for the coupled enzyme reaction at a fixed time and shows a predictable increase in intensity with glucose concentration.

C. Conclusions

Lessons gleaned from nature clearly point towards the biological cell as a model system for carrying out a multitude of functions. While it is a tremendous endeavor to synthetically engineer and build all of the complexities of the cell into a synthetic system from the bottom-up, basic physical aspects of cell design can be replicated in synthetic nanoengineered systems. Here, the concepts of controlled flux and scaled transport drive the design of synthetic reaction vessels which can eventually be used to contain and create more complex networks. One can envision reaction systems akin to synthetic gene regulatory networks as described in synthetic biology pursuits (see, e.g., Hasty, et al., Nature, 2002, 420, 224-230; and Purnick et al., Nat. Rev. Mol. Cell. Biol., 2009, 10, 410-422). The flux of material into or between chambers could be tailored to modulate the level of feedback between systems or to allow response to changes in the local environment. Using multi-scale fabrication techniques to create ensembles of addressable, nanoporous, cellular-scale reactors allows the retention of larger species that represent information or functionality within a reaction system while allowing materials and energy to freely traverse the porous membrane. Such reaction vessels may prove useful in fundamental studies of protein-based complex reaction systems and will enable the development of responsive sensors and therapeutic platforms that rely upon the on-demand conversion or production of biological materials.

Thus, the invention has applications in assembly and testing of genetic networks. The invention also has applications in enzyme kinetic assays, parallel analysis of site directed mutants, enzyme activity screening, protein production, and containment of biological cells.

Example II

Figure 9:
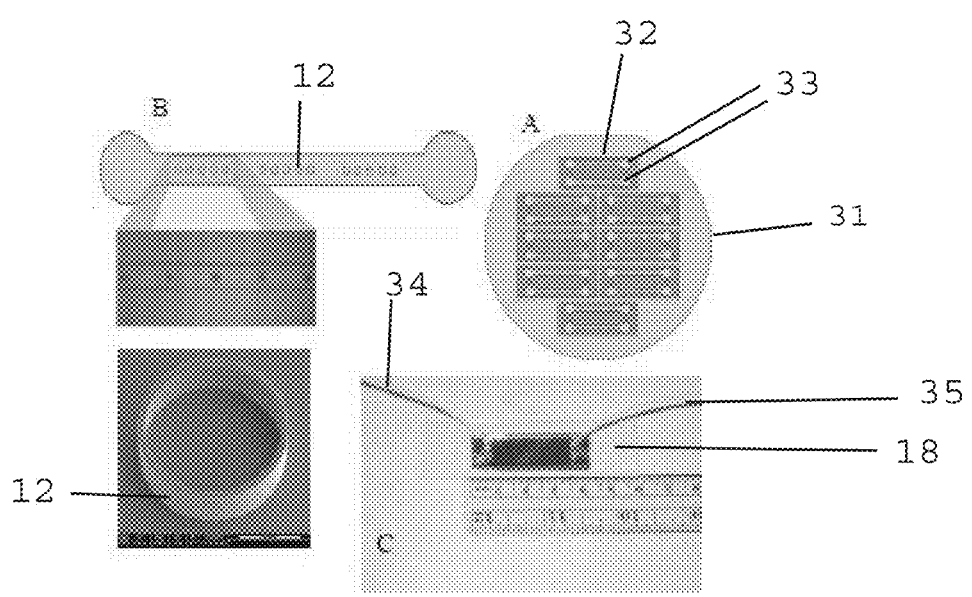
FIG. 9 shows a wafer with several chips and sealed device according to an example version of the invention.

In Example II, microfabrication and nanotechnology based techniques were used to create robust reaction containers from inorganic materials. The small volume devices can be used for a variety of applications including: high throughput screening, enzyme kinetics, analysis of single cells, and cell-free protein synthesis. They can be patterned in different materials, shapes and pore sizes and can be physically or chemically modified to control the flux of molecules of different sizes and charges so that they mimic some of the characteristics of a natural cell. A silicon based device is described in Example II. It can be used for studying biochemical reactions and the effects of scale and compartmentalization on reaction efficiency. The non-limiting example cylindrical container is 2 μm thick with 8 sets of 7 slits spaced around the perimeter. Slits are etched in the same processing step as the device and can range in size from 30-200 nanometers wide and 10 μm deep (see FIGS. 9 and 10). Devices can be created without slits as well. These small volume containers can be used to characterize reaction systems and material organization in a fluid environment. They can also be used to "self assemble" reaction systems. Further, the device allows for controlled transport between the local environment and the contained volume through the synthetic membrane. Cell-free transcription and translation reactions conducted in this container would be useful for producing functional proteins as needed for biomedical applications.

In Example II, there is reported the use of picoliter volume containers to conduct cell-free protein synthesis. Further, the optimal DNA concentration and the time required for maximal protein yield in the device is determined.

A. Materials and Methods

1. Device Fabrication

Reaction containers were fabricated using semiconductor processing techniques to define membrane characteristics. Feature fabrication was achieved using electron beam and optical lithography, followed by cryogenic etching and plasma enhanced chemical vapor deposition (PECVD) of silicon dioxide. Each fabrication run, resulted in a silicon wafer 31 with eight completed chips 32. Each chip 32 comprises two channels 33 with fifteen containers 12 per channel (See FIG. 9A, 9B). For the experiments described here, the resulting containers 12 have a volume of ~19 pL and are made with either no slits or 200 nanometer slit sizes.

The Sylgard 184 silicone elastomer kit was used to prepare Polydimethylsiloxane (PDMS) which is used to seal the top of the devices. Sylgard 184 silicon base and the curing agent were mixed together in a Petri dish at a 10 to 1 ratio, respectively. The homogeneous mixture was degassed in a desiccator for ~30 minutes until the air bubbles were removed and was later placed in the oven at 70° C. for 60-90 minutes. After baking, PDMS was cut into pieces 18 in the shape of the chip and two holes were created on each end of the channel to allow for the input 34 and output 35 of the reaction mixture (FIG. 9C).

Figure 10:
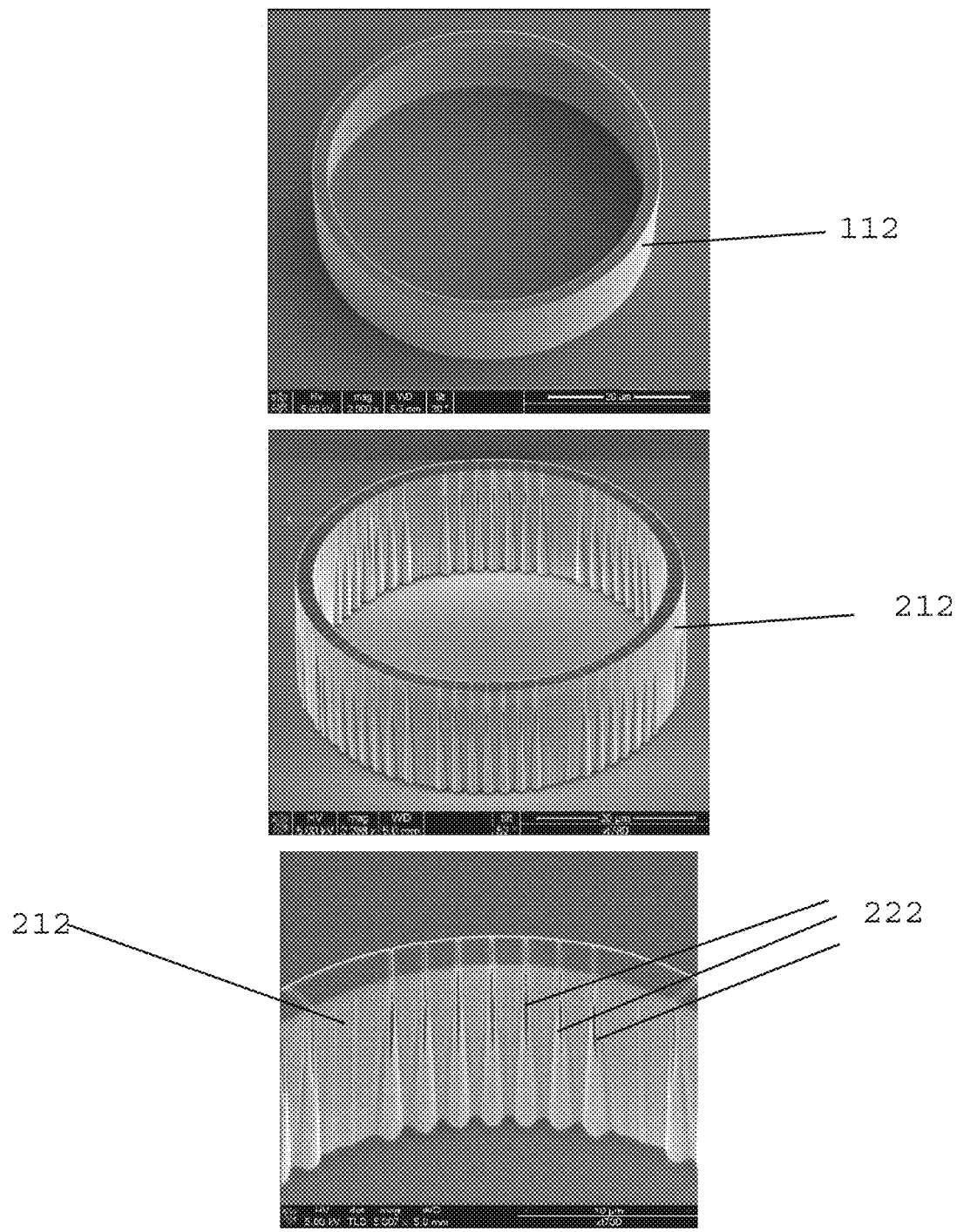
FIG. 10 shows scanning electron microscope (SEM) images of a device according to an example version of the invention wherein the top image is a container with no slits, the middle image is a container with a 200 nanometer slit size, and the bottom image shows the 200 nanometer slits.

FIG. 10 shows scanning electron microscope (SEM) images of a device according to an example version of the invention wherein the top image is a reaction vessel 112 with no slits, the middle image is a reaction vessel 212 with a 200 nanometer slit size, and the bottom image shows the 200 nanometer slits 222.

Figure 10A:
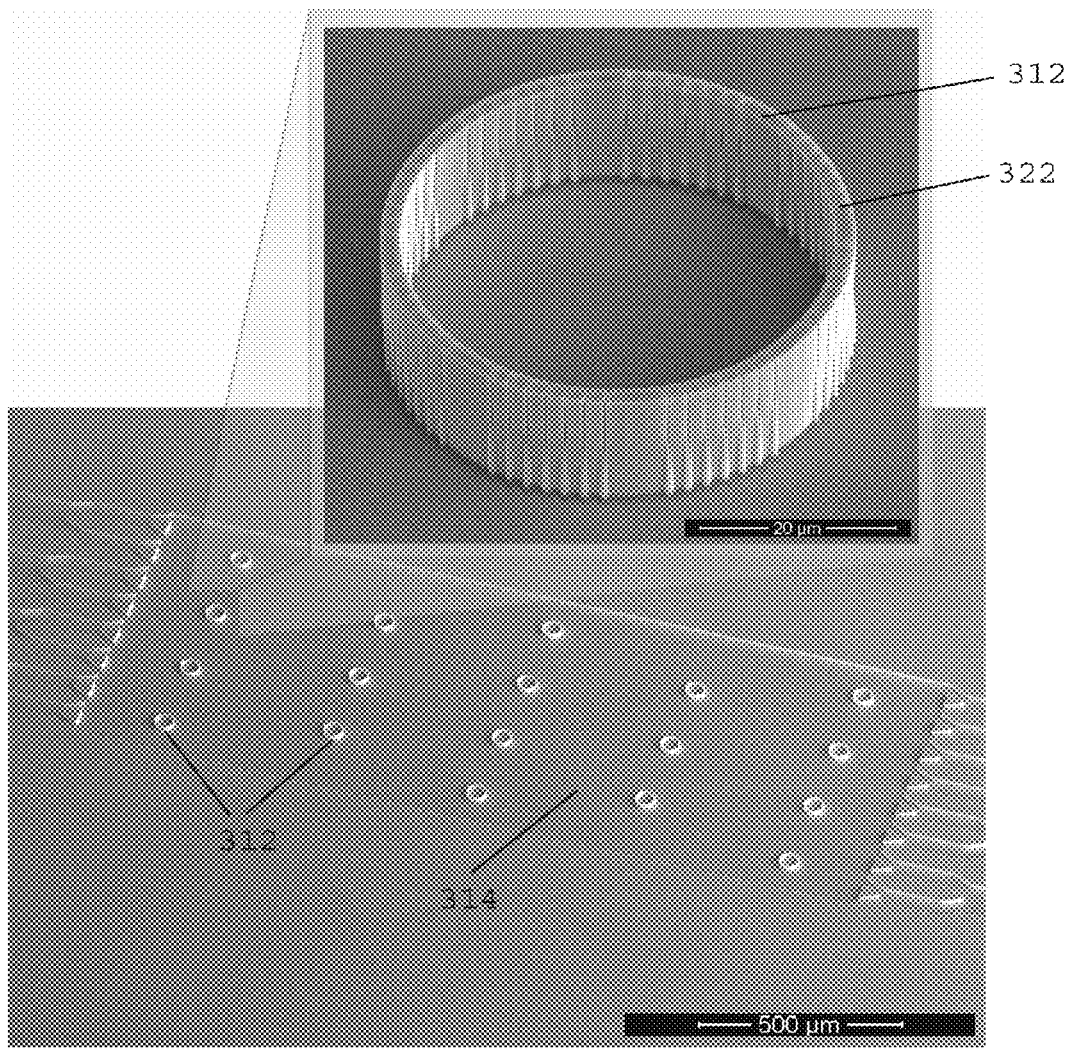
FIG. 10A shows scanning electron microscope (SEM) images of a device according to another example version of the invention wherein the top image is a container with slits, and the bottom image shows a channel with a plurality of the containers.

FIG. 10A shows scanning electron microscope (SEM) images of a device according to another example version of the invention wherein the top image is a reaction vessel 312 with slits, and the bottom image shows a channel 314 with a plurality of the reaction vessels 312.

2. Cell Free Transcription and Translation

*Escherichia coli* (*E. coli*) T7S30 Extract System for Circular DNA reaction kit (Promega TB219) was used for transcription/translation experiments according to the manufacturer's directions. For the template, enhanced green fluorescent protein (eGFP) gene was cloned into pDEST17 (Invitrogen) which allows expression of eGFP from a T7 promoter. The solution containing the DNA template and the cell free transcription/translation mix was mixed in a 1:1 ratio with 8% glycerol and placed in the cell mimic using a glass tip with 2 μm orifice (World Precision Instruments, TIP2TW1). After the structures were loaded, the chip was covered with a 5 millimeter thick layer of PDMS. The channel was then filled with *E. coli* S30 cell free extract and small metabolites. The experiment was incubated at 37° C. EGFP fluorescence was visualized using a Zeiss Axioskop 2 FS Plus epifluorescent microscope.

A similar procedure was also followed for cell-free transcription/translation in containers containing no slits. In this case, the DNA template was mixed with *E. coli* T7S30 cell free extract and small metabolites in a 1:4 ratio, and a final 4 glycerol concentration. The entire reaction mixture was then loaded into the device using a 2 μL glass microtip (World Precision Instruments, TIP2TW1). Several mimics were filled with *E. coli* T7S30 cell free extract and were used as negative controls. The chip was then covered with PDMS and fluorescence was measured. The experiment was incubated at 37° C.

In order to compare cell-free translation in the device with conventional scale reactions, cell-free translation was also conducted in a Costar 96 flat bottom well plate. The concentrations and temperature were kept the same as in the device reactions. The final reaction volume in the plate well was 50 μL and fluorescence was measured every 10 minutes using a Perkin Elmer HTS 7000 Plus BioAssay Reader.

3. Characterization

A GFP standard was prepared by diluting purified GFP protein to concentrations of 26.2, 13.1, 6.55, 3.275, 1.64, 0.82, 0.41, 0.205 and 0.103 μM GFP. Each of the GFP solutions contained 4% glycerol concentration. These solutions were loaded in no pore devices and fluorescence was measured using identical settings for devices with no pores or with 200 nanometer pores. GFP concentration produced in the cell-free transcription/translation reactions in the no slit and 200 nanometer slit size mimics was measured against this GFP standard.

For all the experiments, images were taken every 10 minutes using a dry 40× objective at an exposure time of 500 milliseconds. A 3CC syringe with a 19 gauge needle was used to flow the reaction mix into the channel.

B. Results and Discussion

To test the ability of the microfabricated picoliter volume containers to carry out biochemical reaction systems, cell free protein synthesis experiments using no slits, 200 nanometer slit size devices (see FIG. 10) and 10 nm slit size devices were carried out. Due to the low viscosity of the reaction mix and the small volume of the container (19 pL), we encountered several difficulties when loading the device. These difficulties included overflowing the device at the time of loading, air bubble formation inside the device and quick drying of the sample immediately after loading. In order to overcome these difficulties, the reaction was mixed with different solutions that altered viscosity and evaporation time. The solutions that were evaluated include: polyethylene glycol (PEG), 1% alginate, glycerol, dimethyl sulfoxide (DMSO), agar, dimethylformamide (DMF) and several sucrose concentrations. All these solutions increased viscosity of the reaction mix making it easier to load the devices. Evaporation of the reaction mix after loading the device was also overcome. Protein production was also evaluated and it was significantly decreased. In many cases it was completely inhibited. Alginate was the only solution of those tested that increased protein yield, however it was difficult to handle when loading the device as cross-linking of the mixture would often occur. The most useful solution which did not significantly decrease cell free transcription/translation was glycerol. There was a small decrease in protein yield when using glycerol, but the increased viscosity made it easier to load the device and air bubble formation was avoided. Therefore, several glycerol concentrations were tested and the lowest one which still allowed effective loading of the devices and avoided evaporation was determined to be 4% glycerol concentration.

Figure 11:
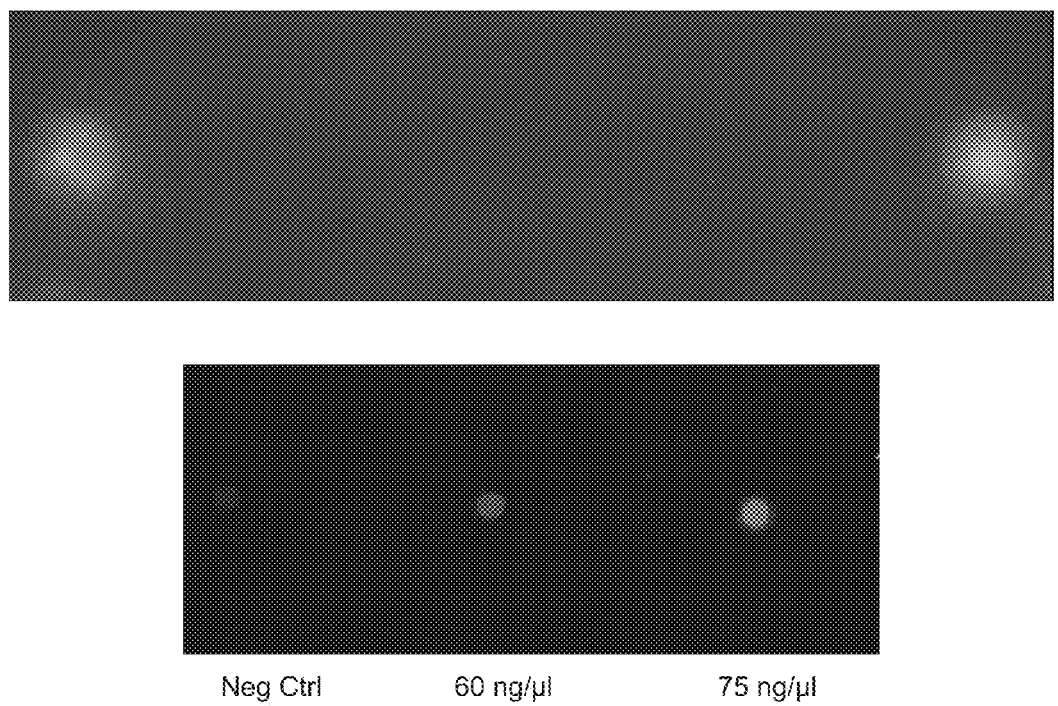
FIG. 11 shows cell-free translation in cell mimic devices according to an example version of the invention wherein the top image is a container with a 200 nanometer slit size and the bottom image is a no slit container.
Figure 12:
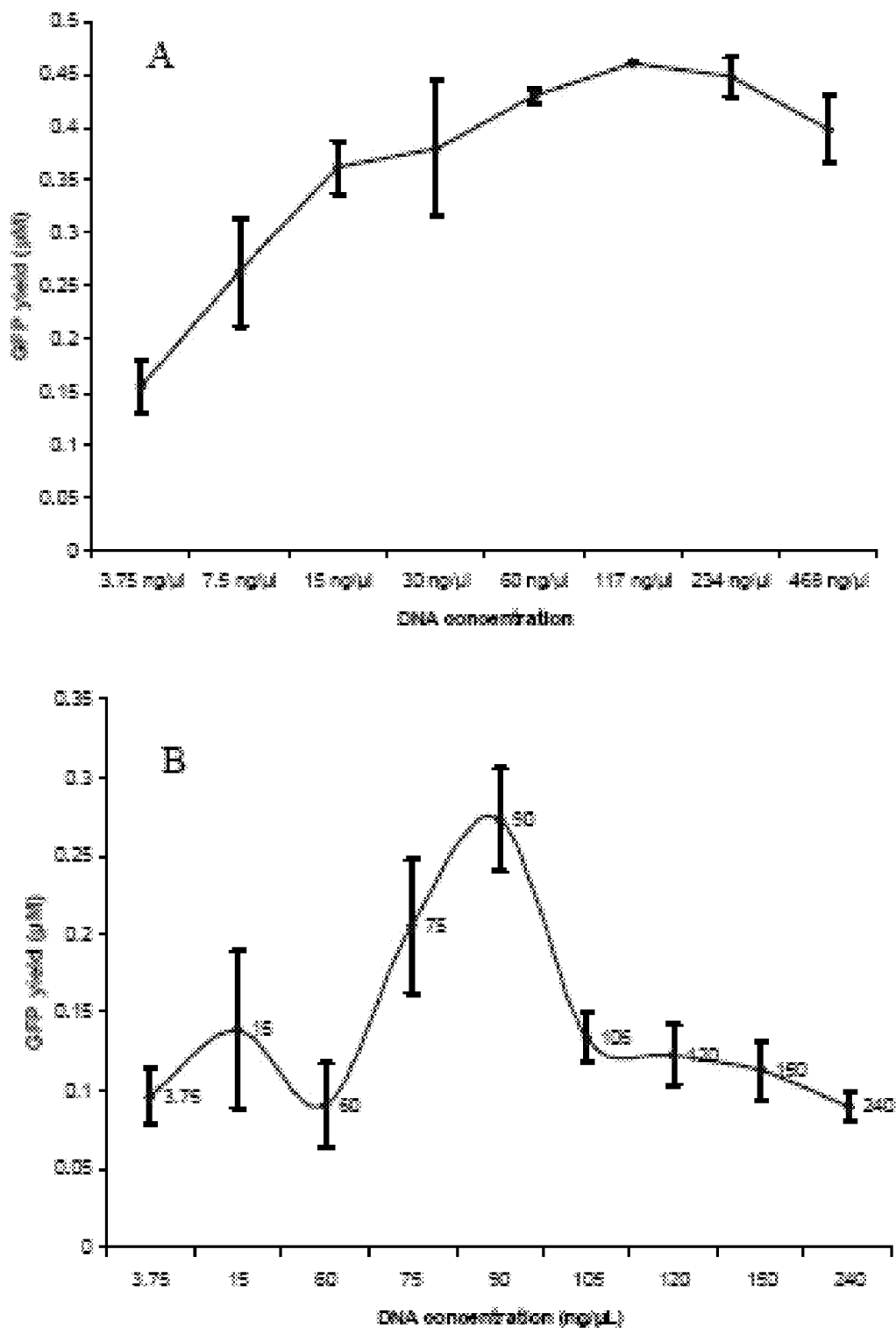
FIG. 12 shows cell-free protein expression in (A) plate reader and (B) a no slit device.

Cell-free transcription/translation experiments were successful for small volume containers that contained no slits and 200 nanometer slits (FIG. 11). The reaction yield was consistent in the no slit devices and the optimal DNA concentration was determined. It was found that 90 ng/μL DNA concentration had the highest GFP yield (FIG. 12) followed by 75 ng/μL. The other concentrations tested had a similar GFP yield of ~0.1 μM. When compared to experiments carried out at the conventional scale (50 μL), a plateau was reached at template concentrations greater than 60 ng/μL (see FIG. 12).

Cell-free transcription/translation in 200 nanometer slit size cell mimic devices was more difficult to achieve and typically GFP was produced throughout the entire microfluidic channel. This could be caused by (a) GFP leaking out of the device through the slits after it was produced or (b) the mRNA leaking out and translation occurring in the channel instead of only in the device. GFP observation in the channel was eliminated when the buffer was flowed through the channel using gravity. Under these conditions, GFP was detected only in the reaction chamber (see FIG. 11 top).

Long periods of protein synthesis were achieved using devices with 10 nm slits and flowing S30 Premix Plus through the microfluidic channel surrounding the cell mimic devices. The S30 Premix Plus contains an ATP-regeneration system, amino acids, tRNAs, rNTPs and appropriate salts needed for protein production. Diffusion of these materials into the cell mimic devices replenishes essential metabolites needed for cell free protein synthesis. Flow rates of 1, 5, 10 and 20 μL/hr were examined and 5 μL/hr was found to be optimal. Slower flow rates were difficult to maintain for long periods using the syringe pump-based pumping system while higher flow rates needlessly consumed materials.

Figure 12A:
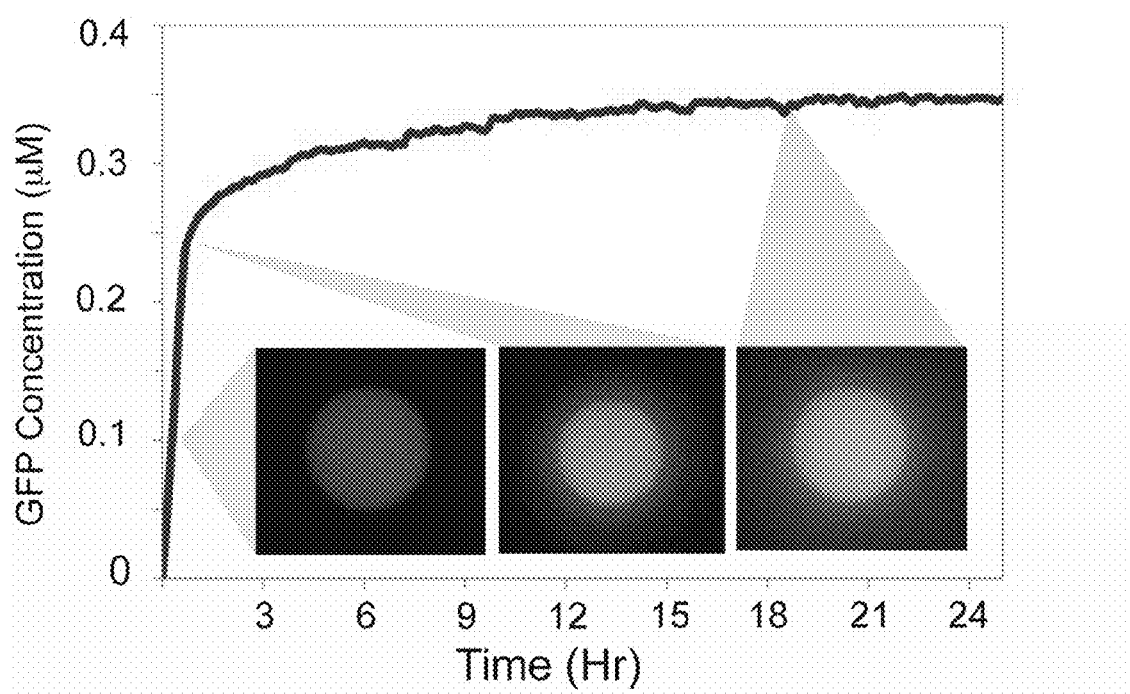
FIG. 12A shows protein synthesis as GFP concentration as a function of time in a cell mimic device containing 10 nanometer slits.

The eGFP protein concentration in a cell mimic device, as determined from fluorescent imaging and comparison to standards, was found to increase for the first 1-2 hours and then reached a plateau that was maintained for the next 24 hours. See FIG. 12A. The maximum concentration observed in the cell mimic device was 0.38 μM. Continuous protein production is observed for up to 25 hours and is likely enabled by the efficient diffusion-based mixing and the feeding/removal of metabolites and harmful byproducts enabled by the membrane. Protein production is continuous as small amounts of protein are observed to leak from the device.

C. Conclusions

Nanotechnology based devices are finding inspiration from biological systems. The cell membrane defines volume (concentration) and controls presentation and release of materials. Molecular networks gather input, perform signal amplification, perform logic, generate output and metabolize energy.

A cell mimic is a potentially uniform platform for sensing, actuating, generating energy, computing, and interfacing to natural systems. The cell membrane can be replaced with synthetic micro- and nano-fabricated structures, such as the structures of the invention, that define cell size, and predictably control material flux. Molecular networks can be replaced with DNA based instructions that modulate gene copy number, control codon usage, and cross reactivity, and provide for cell free transcription/translation. The invention provides a starting point for understanding integrated systems, the effect of scale on network function, and the creation of practical devices. Described in Example II are cell mimic devices that can be used to carry out basic biochemical reactions that are used to translate DNA into RNA and into protein based on DNA encoded instructions. In the future, this device can be used to probe and manipulate biological systems and to perform new functions. It can also be used to carry out enzymatic reactions in order to better understand molecular systems and self organization at the micro scale.

Example III

Figure 13:
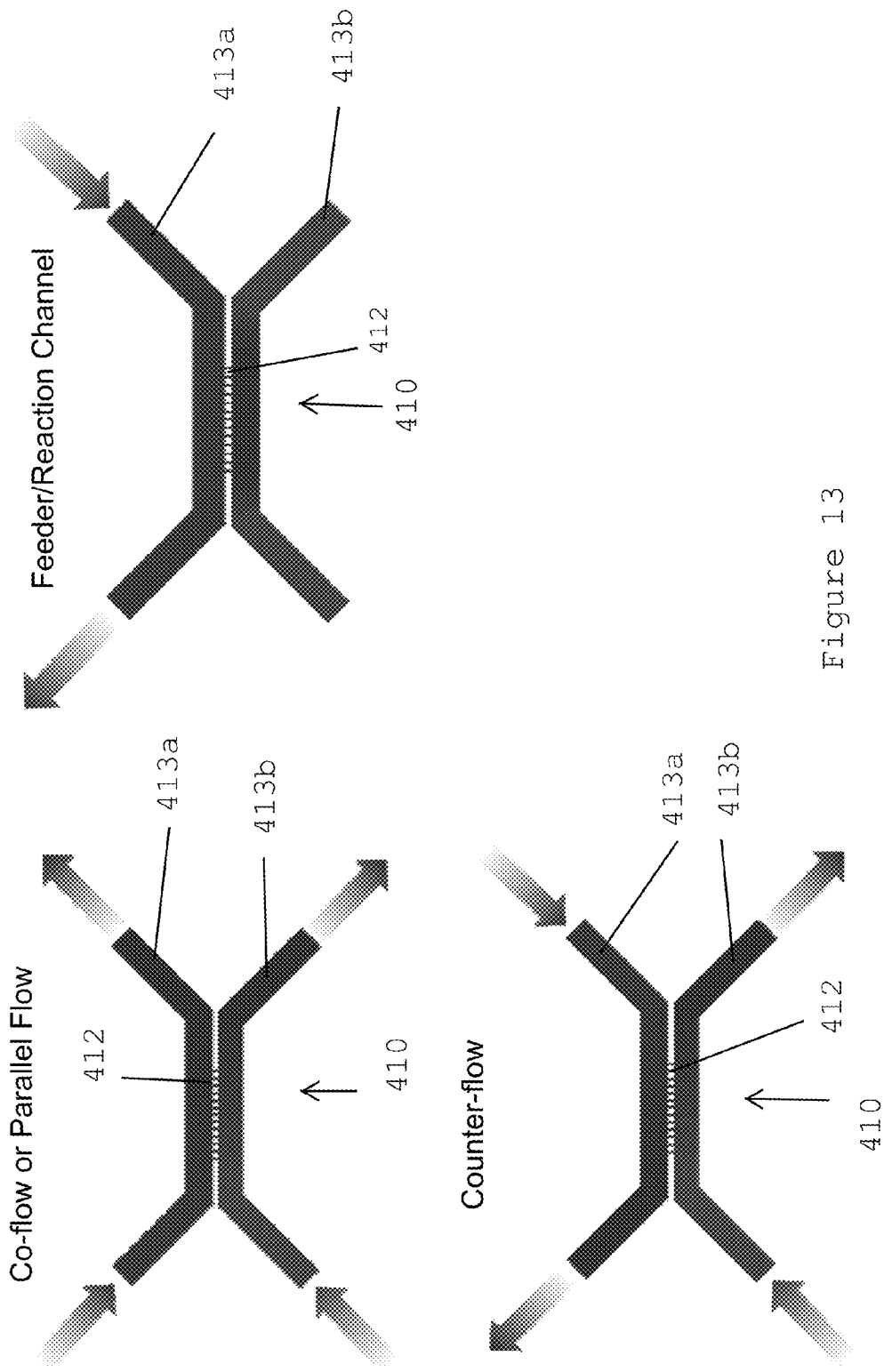
FIG. 13 shows flow in a device according to another example version of the invention.

FIG. 13 shows flow in a device 410 according to another example version of the invention. The relative flow rates, and direction of flow can be controlled individually in each microchannel 413a, 413b to achieve the desired chemical gradients. In all cases, the transfer of molecules between channels is driven primarily by diffusion. Momentum transport, e.g. hydrodynamic flow, is minimal across the nanoporous membrane 412 that separates the two microchannels 413a, 413b.

Figure 14:
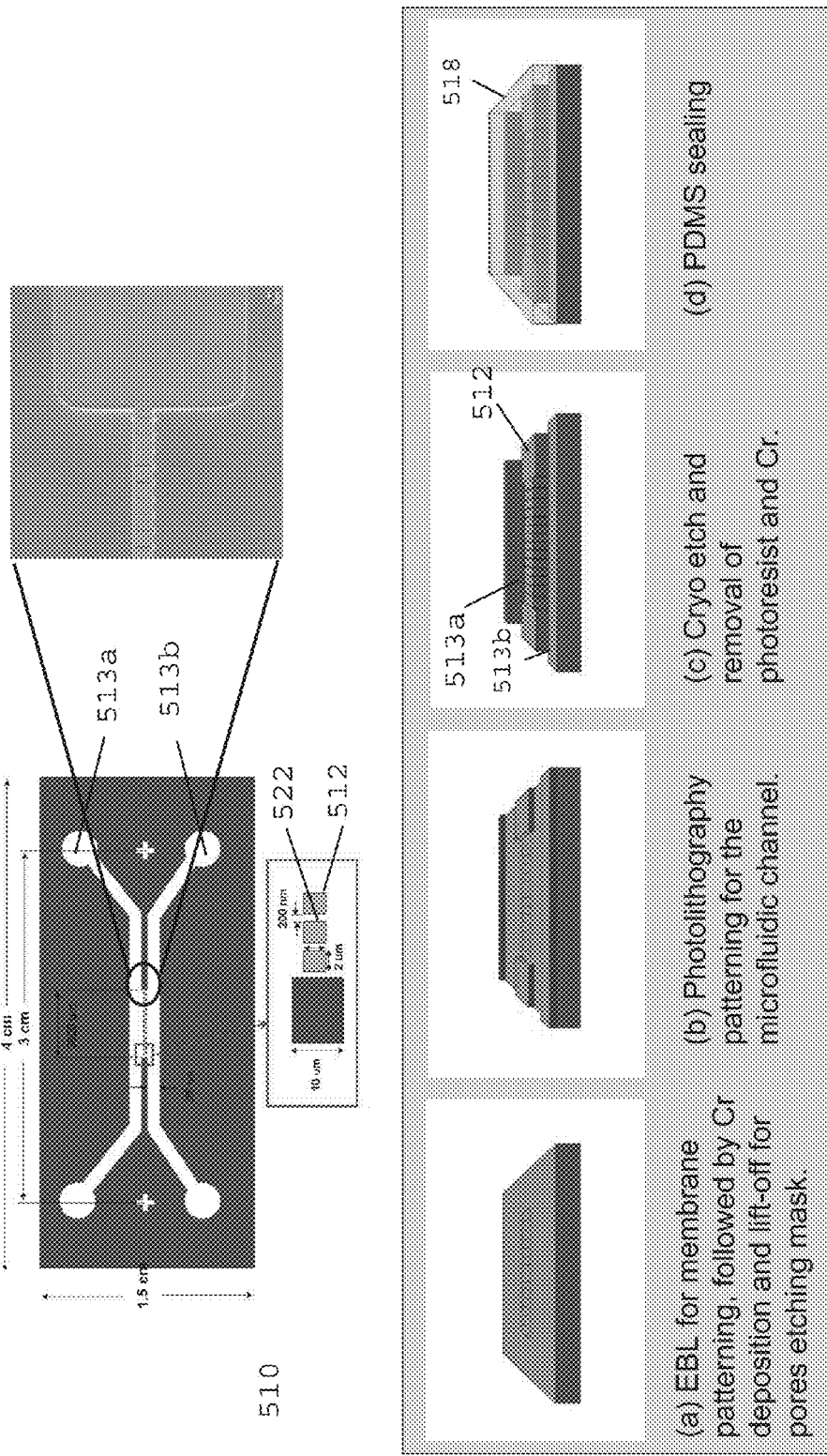
FIG. 14 shows the steps in fabrication of another membrane according to the invention.

FIG. 14 shows the steps in fabrication of another structure 510 according to the invention. In Step (a) electron beam lithography is used for membrane patterning, followed by chromium deposition and lift-off for the pore etching mask. In step (b), photolithography patterning is used for the microfluidic channel. In step (c), cryogenic etch and removal of photoresist and chromium is undertaken. In step (d), PDMS sealing occurs with a cover 518. The structure 510 has two microchannels 513a, 513b separated by a nanoporous membrane 512 having a length of about 3600 micrometers, a width of 2 micrometers, and transverse pores 522 in the form of rectangular slits with a width of 200 nanometers. The pores 522 are spaced apart a distance of 2 micrometers. The microchannels 513a, 513b are 200 micrometers wide in FIG. 14.

Figure 15:
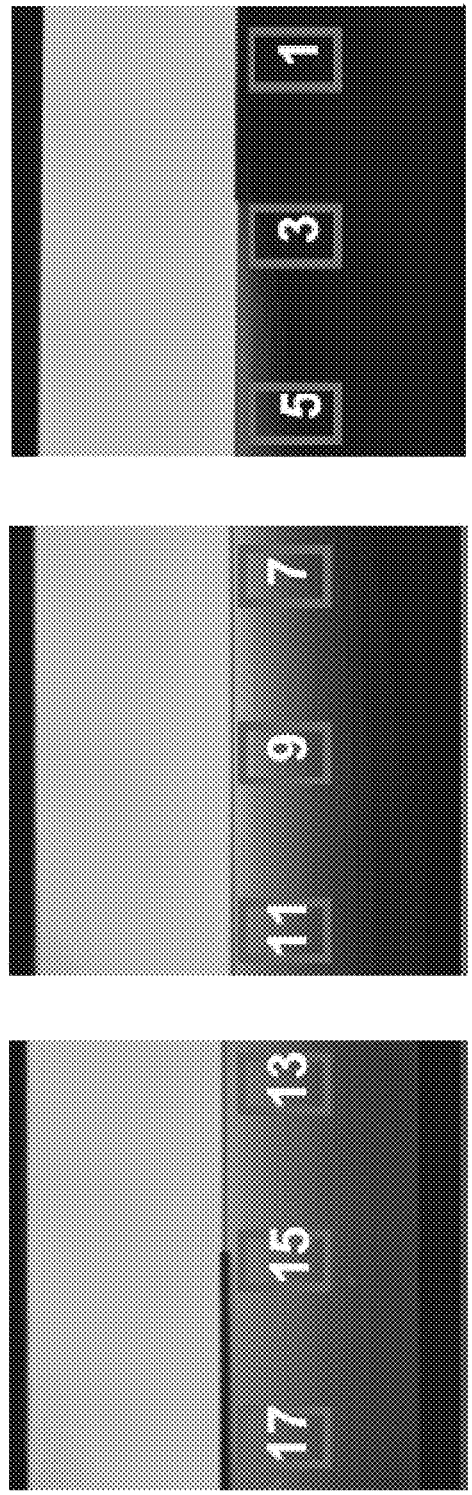
FIG. 15 shows photographs depicting molecular exchange across a membrane of FIG. 14.

FIG. 15 shows photographs depicting molecular exchange across a membrane of FIG. 14. The upper channel is loaded with fluorescein (10 μM) while the lower channel is loaded with buffer. Operating at ~0.1 μL/min, diffusion mediated transport is evident across the membrane, as fluorescence intensity in the lower channel increases from the channel inlet [1] towards the outlet [17].

A membrane such as shown in FIG. 14 can be used to understand chemical signaling and cellular taxis. Cell migration (motility, taxis) resulting from perturbations in the local environment may initiate shifts in microbial abundance and diversity. Some keys to understanding the fundamental roles that taxis and transport may play in cell physiology include (i) the nature, magnitude, and extent of chemical shift, (ii) the strength, speed, and variation of the response, and (iii) the physical composition of the local environment. Traditional assays, such as swarm plates and capillary assays have limitations, such as (i) average properties of a population, (ii) limited control of the chemical environment, and (ii) these assays are primarily quantitative. The present invention provides tools that allow for the rapid and quantitative screening of new isolates to better understand their response to specific plant metabolites.

Figure 16:
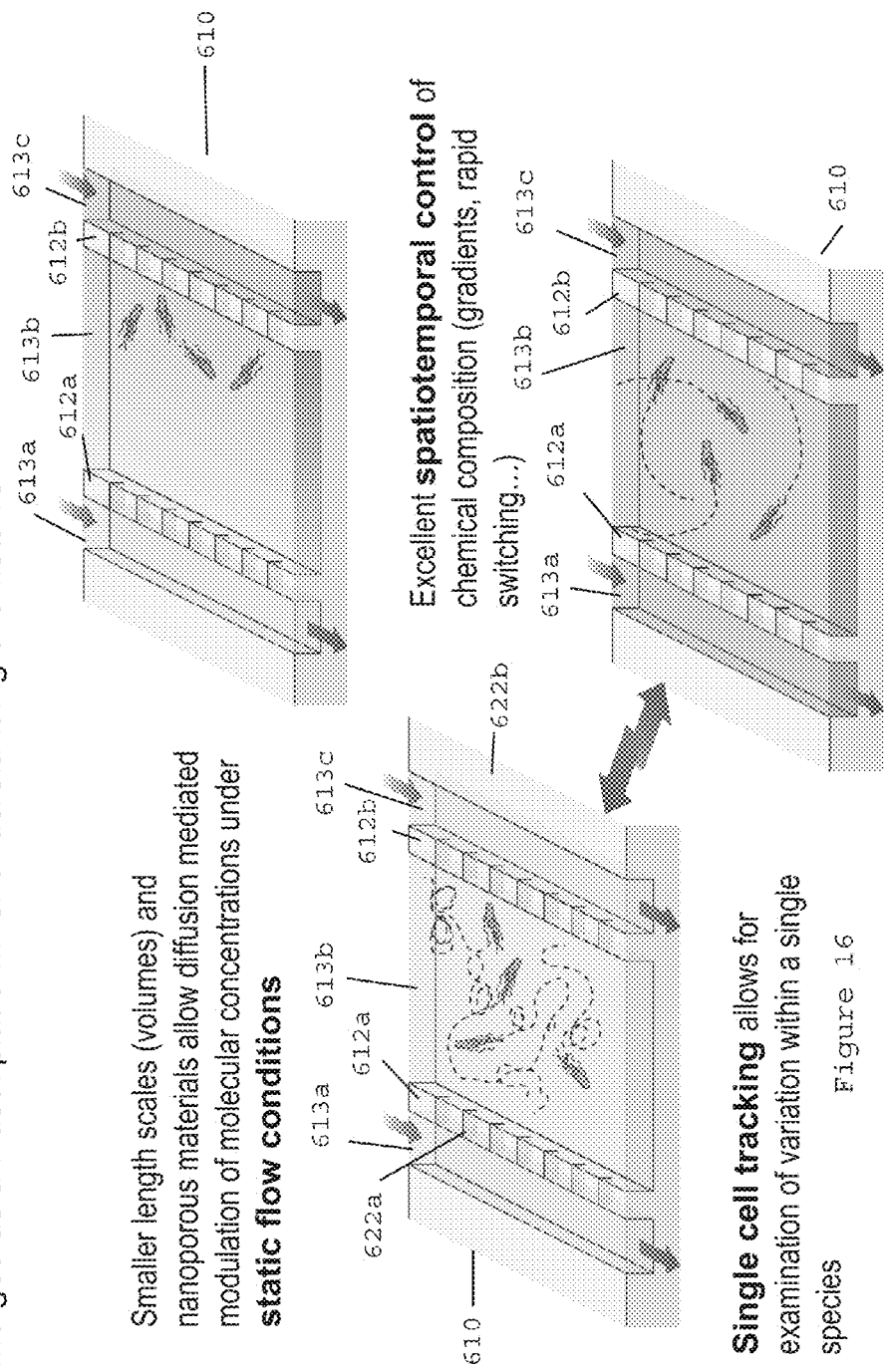
FIG. 16 shows another membrane according to the invention useful for understanding microbial and mammalian chemotaxis.

As shown in FIG. 16, microfluidics is a powerful tool for interfacing with biological systems and has emerged as an ideal platform for understanding chemotaxis. Smaller length scales (volumes) and nanoporous materials allow diffusion mediated modulation of molecular concentrations under static flow conditions. Excellent spatiotemporal control of chemical composition (gradients, rapid switching . . . ) is afforded. Single cell tracking allows for examination of variation within a single species. The structure 610 has three microchannels 613a, 613b, 613c separated by nanoporous membranes 612a, 612b with slits 622a, 622b.

Figure 16A:
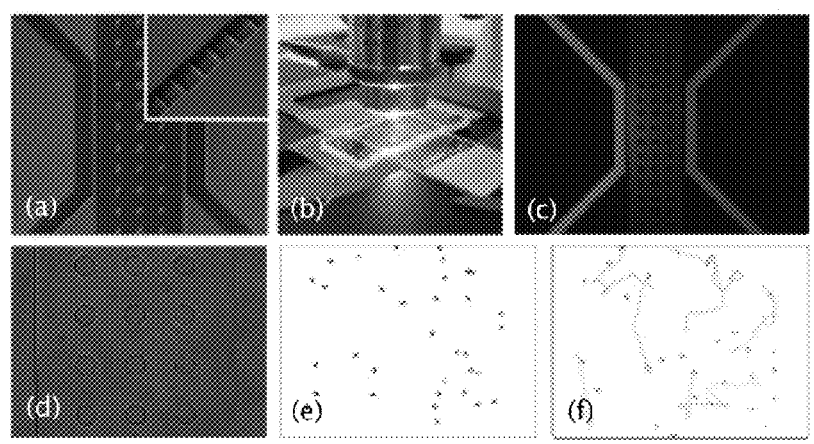
FIG. 16A shows that nanostructured silicon masters (a, inset shows barrier) were used to mold and assemble silicone microfluidic structures with nanoporous barriers (b) and used to study molecular transport of fluorescent molecules (c). Microbial motility (d-f) was recorded and tracked within this platform.

FIG. 16A shows that nanostructured silicon masters (a, inset shows barrier) were used to mold and assemble silicone microfluidic structures with nanoporous barriers (b) and used to study molecular transport of fluorescent molecules (c). Microbial motility (d-f) was recorded and tracked within this platform.

Figure 17:
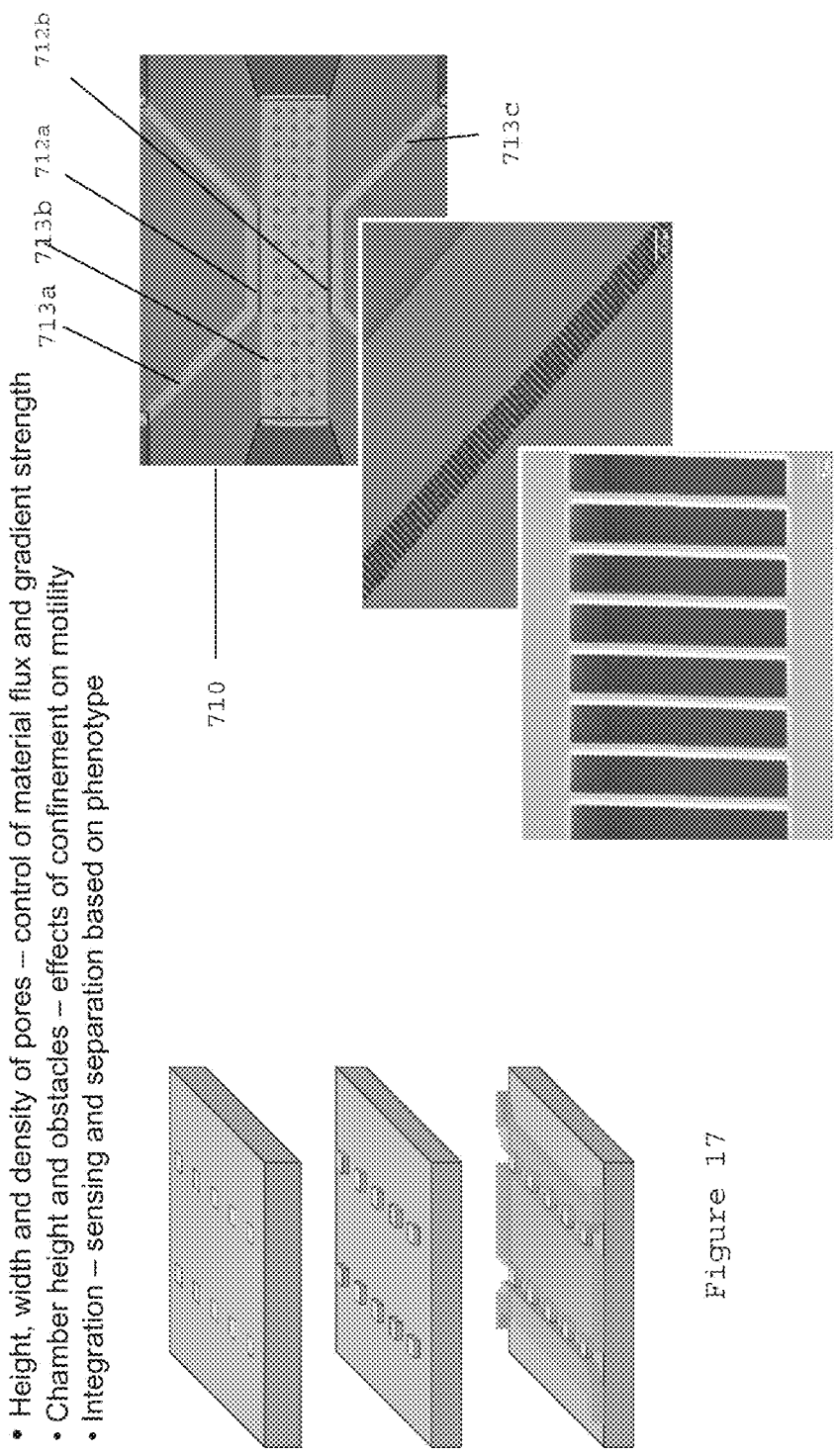
FIG. 17 shows various stages in a fabrication of a membrane according to the invention.

FIG. 17 shows various stages in a fabrication of a membrane according to the invention. A combination of electron beam and photolithographic patterning complemented with anisotropic silicon etching (as in Examples I and II) allows for device features to be tailored based on the demand of different experiments. The height, width and density of pores provides control of material flux and gradient strength. The chamber height and obstacles provide insight on the effects of confinement on motility. Integration provides sensing and separation based on phenotype. The structure 710 has three microchannels 713a, 713b, 713c separated by nanoporous membranes 712a, 712b with slits.

Figure 17A:
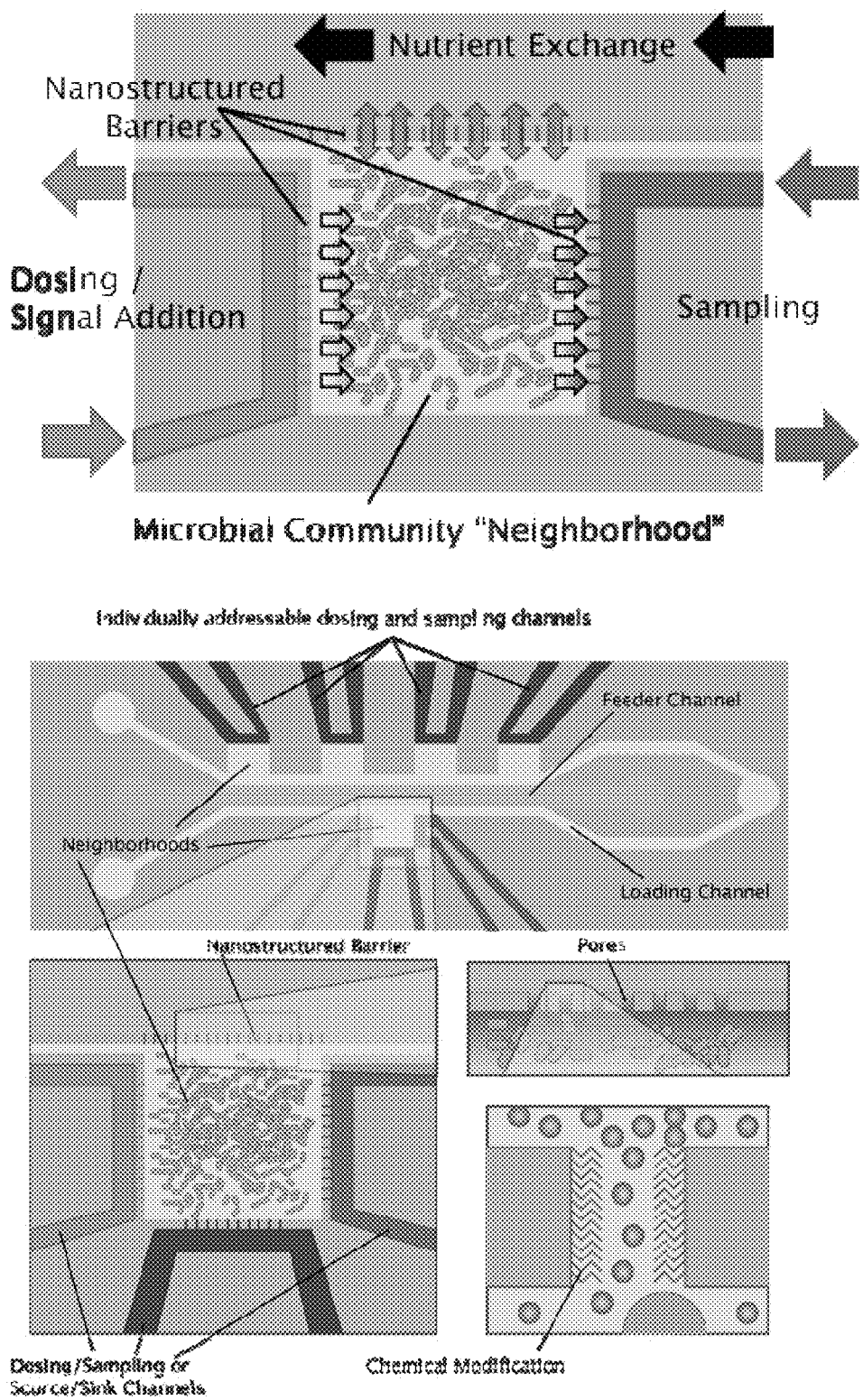
FIG. 17A shows single neighborhood and divided neighborhood co-cultures of "sender"-"receiver" cultures used to quantify community dynamics and shows that multiscale aspects of the proposed platform lead to functionality across the molecular, cellular and multi-cellular length scales.

The top drawing in FIG. 17A shows single neighborhood and divided neighborhood co-cultures of "sender"-"receiver" cultures used to quantify community dynamics. The bottom drawing in FIG. 17A shows that multiscale aspects of the proposed platform lead to functionality across the molecular, cellular and multi-cellular length scales.

Figure 18:
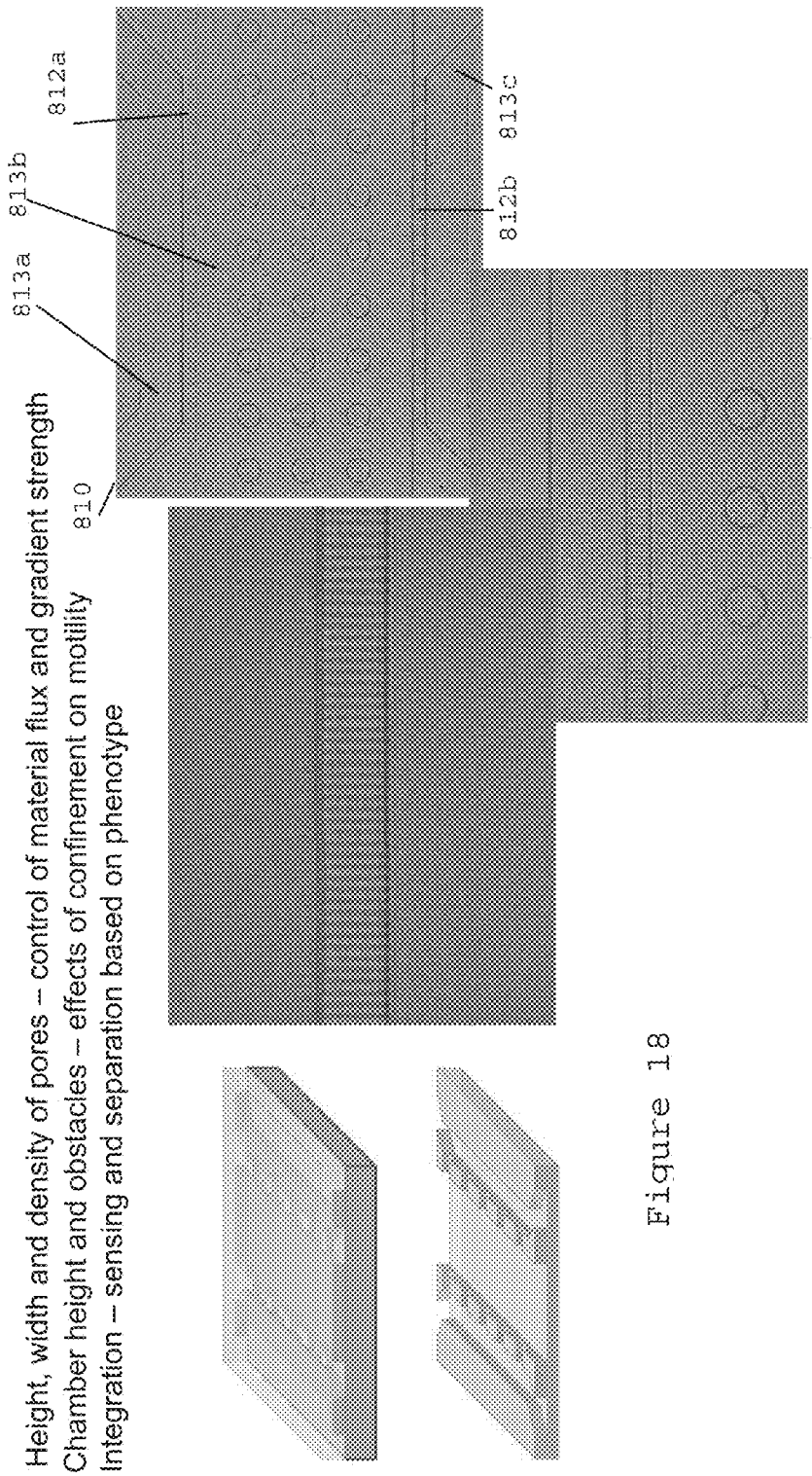
FIG. 18 shows various stages in a fabrication of a membrane according to the invention.

FIG. 18 shows various stages in a fabrication of a membrane according to the invention and includes similar features to FIG. 17. These membranes according to the invention provide optimization of imaging and tracking and analysis. The structure 810 has three microchannels 813a, 813b, 813c separated by nanoporous membranes 812a, 812b with slits.

Figure 18A:
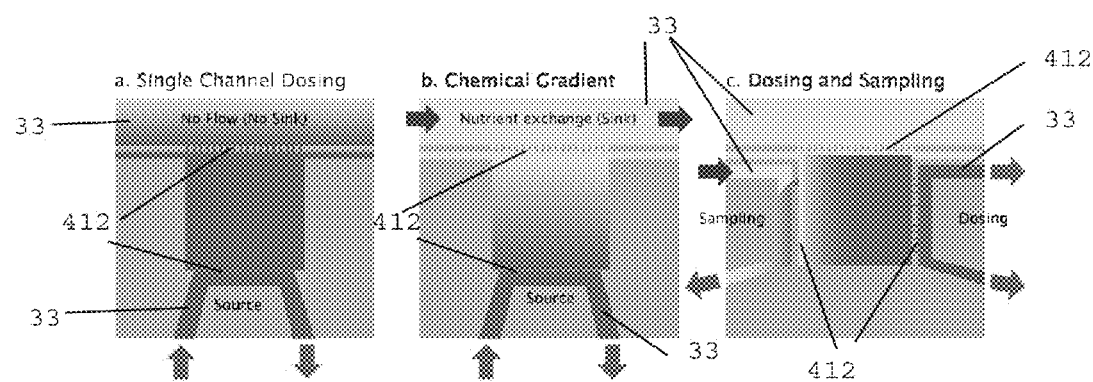
FIG. 18A shows that variability in channel geometry, barrier composition, and fluid flow will allow accessibility to a variety of functional configurations that can be used to modulate and measure local chemical signals in real time.

FIG. 18A shows that variability in channel geometry, barrier composition, and fluid flow will allow accessibility to a variety of functional configurations that can be used to modulate and measure local chemical signals in real time.

Figure 19:
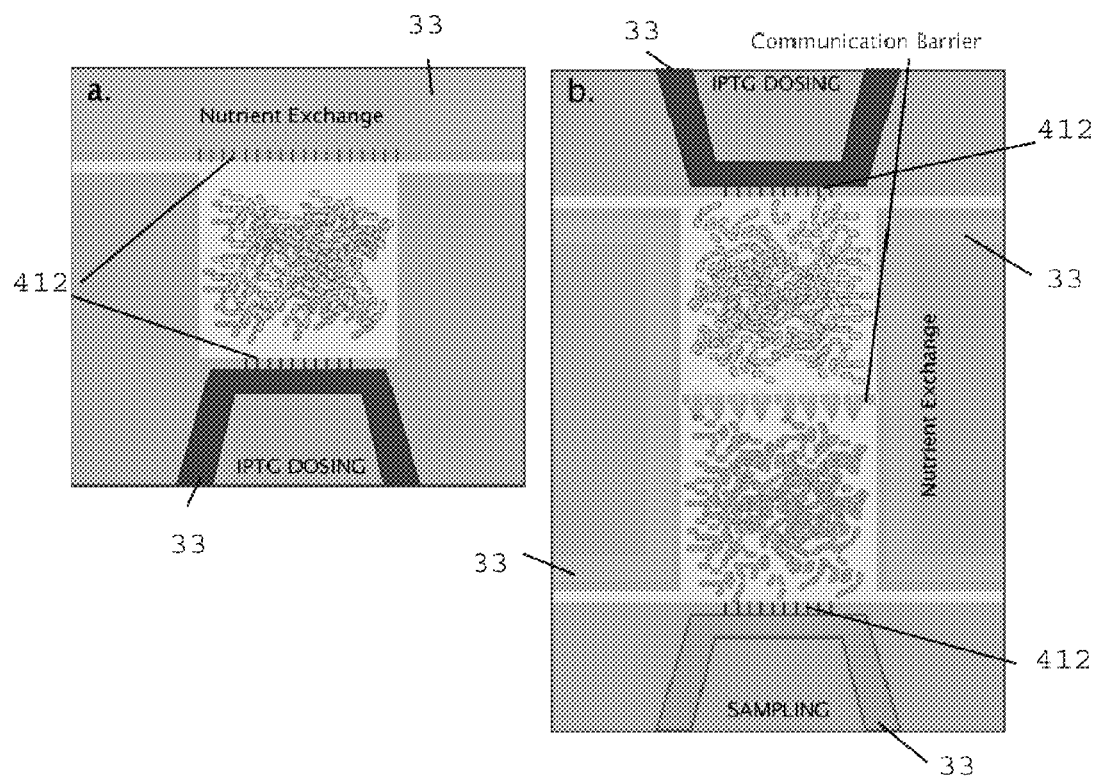
FIG. 19 shows how single neighborhood and divided neighborhood co-cultures of "sender"-"receiver" cultures will be used to quantify community dynamics.

FIG. 19 shows how single neighborhood and divided neighborhood co-cultures of "sender"-"receiver" cultures will be used to quantify community dynamics wherein IPTG is isopropyl-beta-D-thiogalactopyranoside.

In Example III, the membrane has been formed in a straight line or lines to separate two or more regions or microchannels. This allows molecular exchange between two or more microfluidic channels in which one or more channels constitutes a reaction or observation channel in which no hydrodynamic flow occurs. This "no flow" or "zero flow" channel is similar to the reaction vessels of Examples I and II. In Example III, there is demonstrated a reaction vessel or channel, in which direct pumping or flow of fluid does not occur, but instead transport into the reaction vessel or channel occurs through the membrane architecture.

The nanotechnologies of the present invention provide enabling tools for understanding biological function and design such as (i) interfacing at the molecular and cellular level, (ii) mimicking cell structures for simplifying biological complexity, and (iii) examining hypotheses about biological systems that cannot be readily tested in biological systems. This can lead to the development of devices useful for understanding system design and the effect of scale on biomolecular system function such as (i) biomedical sensing and actuation, (ii) biochemical transformations (bioenergy), and (iii) synthesis of specialty chemicals through metabolic processes.

Structures of the present invention can provide cell mimic structures. They can be prepared as isolated cells or arrays of cells. They provide an appropriate physical environment for testing re-created biochemical networks. They can arbitrarily change the volume or porosity defined by the reaction vessel. These small volume reaction containers provide screening systems (arrays without surface bound elements) and caging cells.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims is not limited to the embodiments contained herein.

What is claimed is:

1. A structure for controlling transport of a material, the structure comprising:
   a side wall and an end wall at least partially defining a first volume and a second volume, the side wall separating the first volume and the second volume, the side wall including a plurality of pores extending from a first surface facing the first volume to a second surface facing the second volume thereby providing a transport path between the first volume and the second volume, the pores having a limiting aperture in the range of 1 to 500 nanometers, the pores having a length of 5000 micrometers or less, wherein the end wall and the side wall are monolithic being created by etching a substrate; and
   a material located within the first volume or within the second volume, the material having a physical or chemical property such that the material is selectively restricted by the pores from passing from the first volume to the second volume or from passing from the second volume to the first volume; and
   means for controlling transport of the material both into and out of the first volume,
   wherein the substrate comprises a substrate material, and
   wherein the end wall and the side wall comprise the substrate material.

2. The structure of claim 1 wherein:
   bidirectional transfer of the material between the first volume and the second volume is driven by diffusion.

3. The structure of claim 2 wherein:
   the material is selected from nucleic acids, proteins, enzymes, metabolites, cell extract, and biological cells.

4. The structure of claim 1 wherein the means for controlling transport of the material comprises a physical or chemical coating on an inner surface of the pores.

5. The structure of claim 4 wherein the coating changes volume upon application of a signal to the coating.

6. The structure of claim 5 wherein the signal is chemical, biological, electrical or optical.

7. The structure of claim 1 wherein:
the side wall has a thickness in the range of 0.5 to 5 micrometers.
8. The structure of claim 1 wherein:
the limiting aperture is in the range of 1 to 200 nanometers.
9. The structure of claim 1 wherein:
the side wall has a shape selected from polygonal, circular, elliptical or oval.
10. The structure of claim 1 wherein:
the side wall has a circular shape and has an inside diameter in the range of 1 to 100 micrometers.
11. The structure of claim 1 further comprising:
a second end wall in contact with the side wall, the second end wall further defining the first volume and the second volume,
wherein the second end wall comprises a cover.
12. The structure of claim 11 wherein:
the cover comprises a silicone.
13. The structure of claim 1 further comprising:
a second side wall further defining the first volume to form a channel structure.
14. The structure of claim 1 further comprising:
a third side wall further defining the second volume to form a channel structure.
15. The structure of claim 1 wherein:
the side wall includes a first end and a second end, and
a length from the first end to the second end ranges from 10 to 100 micrometers.
16. The structure of claim 1 wherein:
the pores comprise a generally rectangular slit.
17. The structure of claim 1 wherein:
the substrate comprises silicon.
18. The structure of claim 1 wherein:
the first volume contains a first material,
the second volume contains a second material reactive with the first material, and
at least one of the first material and the second material can diffuse through the pores.
19. A microfluidic device comprising:
the structure of claim 1,
wherein a microchannel is formed in a surface of the substrate, the microchannel defining the second volume, the second volume at least partially surrounding the first volume.
20. The microfluidic device of claim 19 wherein:
the side wall is arranged within the microchannel.
21. A method for manufacturing volume defined regions, the method comprising:
(a) providing a substrate having an upper surface;
(b) forming a first etch mask on the upper surface of the substrate, the first etch mask defining a side wall to be formed in the substrate, the first etch mask further defining a plurality of limiting apertures to be formed in the side wall;
(c) forming a second etch mask on the upper surface of the substrate, the second etch mask defining an end wall to be formed in the substrate; and
(d) etching the substrate to create the side wall, the limiting apertures and the end wall wherein the side wall and the end wall partially define a first volume and a second volume, the side wall separating the first volume and the second volume,
wherein the limiting apertures control transport of material both into and out of the first volume, wherein the limiting apertures are in the range of 1 to 500 nanometers.
22. The method of claim 21 wherein:
step (b) comprises forming the first etch mask using electron beam lithography and a metal lift-off process, and
step (d) comprises cryogenically etching the substrate.
23. The method of claim 21 wherein:
the second volume at least partially surrounding the first volume.
24. The method of claim 23 wherein:
the unmasked regions are dimensioned to have a width in the range of 1 to 500 nanometers.
25. The method of claim 20 wherein:
the side wall has a thickness in the range of 0.1 to 5 micrometers.
26. A method for reacting a first material and a second material, the method comprising:
(a) providing a structure for controlling transport of the first material and the second material, the structure comprising a side wall and an end wall at least partially defining a first volume and a second volume, the side wall separating the first volume and the second volume, the side wall including a plurality of pores extending from a first surface facing the first volume to a second surface facing the second volume thereby providing a transport path for the second material between the first volume and the second volume, the pores having a limiting aperture in the range of 1 to 500 nanometers, the pores having a length of 5000 micrometers or less, wherein the end wall and the side wall are monolithic being created by etching a substrate, wherein the first volume contains the first material and the second volume contains the second material; and
(b) allowing the second material to flow through the pores such that the second material reacts with the first material,
wherein the pores control transport of material both into and out of the first volume,
wherein the substrate comprises a substrate material, and
wherein the end wall and the side wall comprise the substrate material.
27. The method of claim 26 wherein:
wherein the second volume is at least partially defined by a microchannel, and
the second material flows through the microchannel before transporting through the pores, the second volume at least partially surrounding the first volume.
28. The method of claim 26 wherein:
the second material reacts with the first material in a reaction controlled by a flux of the second material through the pores.
29. The method of claim 26 wherein:
wherein the first volume is less than 1 nanoliter.
30. The method of claim 26 wherein:
the second material reacts with the first material to produce a protein.
31. The method of claim 26 wherein:
the second material reacts with the first material in an enzymatic reaction.
32. The method of claim 26 wherein:
the first material or the second material comprises a biological sensing element of a biosensor.
33. The method of claim 26 wherein:
step (b) is driven by bidirectional diffusion.

* * * * *